US 7,019,305 B2

(12) United States Patent
Eversmann et al.

(10) Patent No.: US 7,019,305 B2
(45) Date of Patent: Mar. 28, 2006

(54) BIOSENSOR CIRCUIT AND SENSOR ARRAY CONSISTING OF A PLURALITY OF SAID BIOSENSOR CIRCUITS AND BIOSENSOR ARRAY

(75) Inventors: Bjorn-Oliver Eversmann, Munich (DE); Martin Jenkner, Planegg (DE); Christian Paulus, Weilheim (DE); Roland Thewes, Grobenzell (DE)

(73) Assignee: Infineon Technologies AG, Munich (DE)

( * ) Notice: Subject to any disclaimer, the term of this patent is extended or adjusted under 35 U.S.C. 154(b) by 0 days.

(21) Appl. No.: 10/821,803

(22) Filed: Apr. 8, 2004

(65) Prior Publication Data

US 2005/0017190 A1    Jan. 27, 2005

Related U.S. Application Data

(63) Continuation of application No. PCT/DE02/03613, filed on Sep. 25, 2002.

(30) Foreign Application Priority Data

Oct. 16, 2001 (DE) ................................ 101 51 020

(51) Int. Cl.
*G01N 27/416* (2006.01)

(52) U.S. Cl. ............................ 250/370.14; 250/370.11

(58) Field of Classification Search ........... 250/370.14, 250/370.11, 370.13; 435/288.7, 288.2, 288.5, 435/7.1, 8; 436/525, 531, 805
See application file for complete search history.

(56) References Cited

U.S. PATENT DOCUMENTS

| 4,701,253 | A | | 10/1987 | Ligtenberg et al. |
|---|---|---|---|---|
| 4,894,339 | A | * | 1/1990 | Hanazato et al. ........... 435/182 |
| 5,309,085 | A | | 5/1994 | Sohn |
| 5,466,348 | A | * | 11/1995 | Holm-Kennedy ........... 205/775 |
| 5,602,467 | A | | 2/1997 | Krauss et al. |
| 6,060,327 | A | * | 5/2000 | Keen ...................... 204/403.14 |
| 6,117,643 | A | * | 9/2000 | Simpson et al. ............. 435/7.1 |
| 6,326,215 | B1 | * | 12/2001 | Keen .......................... 436/518 |
| 6,546,268 | B1 | * | 4/2003 | Ishikawa et al. ............ 600/345 |

(Continued)

FOREIGN PATENT DOCUMENTS

DE    39 26 657 A1    11/1990

(Continued)

OTHER PUBLICATIONS

Thomas, C.A., et al., "A Miniature Microelectrode Array to Monitor the Bioelectric Activity of Cultured Cells", Experimental Cell Research, 1972, vol. 74, pp. 61-66.

(Continued)

*Primary Examiner*—Otilia Gabor
(74) *Attorney, Agent, or Firm*—Darby & Darby

(57) ABSTRACT

Biosensor circuit arrangement including a substrate, a sensor element formed in or on a surface region of the substrate with a physical parameter, which is coupled to a substance to be examined, the type of coupling having a resistive component, the sensor element having an electrically conductive sensor electrode that is coupled to the substance to be examined, the sensor element having a measuring transistor the gate terminal of which is coupled to the electrically conductive sensor electrode, and the physical parameter being the threshold voltage of the measuring transistor, and a calibration device formed in or on the substrate, the calibration device being set up such that it is used to at least partly compensate for an alteration of the value of the physical parameter of the sensor element.

35 Claims, 19 Drawing Sheets

U.S. PATENT DOCUMENTS

| | | | |
|---|---|---|---|
| 6,602,399 B1 * | 8/2003 | Fromherz et al. | 205/777.5 |
| 6,673,596 B1 * | 1/2004 | Sayler et al. | 435/288.7 |
| 6,699,667 B1 * | 3/2004 | Keen | 435/6 |
| 6,716,642 B1 * | 4/2004 | Wu et al. | 436/518 |

FOREIGN PATENT DOCUMENTS

| | | |
|---|---|---|
| DE | 43 20 881 A1 | 9/1994 |
| WO | WO-01/75462 A1 | 10/2001 |

OTHER PUBLICATIONS

Berdondini, L., et al., "High-Density Microelectrode Arrays for Electrophysiological Activity Imaging of Neuronal Networks", ICECS 2001, pp. 1239-1242.

Enz, Christian C., et al., "Circuit Techniques for Reducing the Effects of Op-Amp Imperfections: Autozeroing, Correlated Double Sampling, and Chopper Stabilization", Proceedings of the IEEE, Nov. 1996, vol. 84, No. 11, pp. 1584-1614.

Gross, Guenter W., et al., "The use of neuronal networks on multielectrode arrays as biosensors", Biosensors & Bioelectronics, 1995, vol. 10, pp. 553-567.

Baumann, W.H., et al., "Microelectronic sensor system for microphysiological application on living cells", Sensors and Actuators B, 1999, vol. 55, pp. 77-89.

Krause, M., et al., "Extended gate electrode assays for extracellular signal recordings", Sensors and Actuators B, 2000, vol. 70, pp. 101-107.

* cited by examiner

BIOSENSOR CIRCUIT AND SENSOR ARRAY CONSISTING OF A PLURALITY OF SAID BIOSENSOR CIRCUITS AND BIOSENSOR ARRAY

CROSS-REFERENCE TO RELATED APPLICATION

This application is a continuation of International Patent Application Serial No. PCT/DE02/03613, filed Sep. 25, 2002, which published in German on May 8, 2003 as WO 03/038420.

FIELD OF THE INVENTION

The invention relates to a circuit arrangement, a sensor array and a biosensor array.

BACKGROUND OF THE INVENTION

The network structure of higher animals' brains is of high complexity and is the subject of current research in neurobiology. One aspect of this complexity can be seen in the fact that outwardly discernible functionalities such as memory or object formation is only realized by the interlinking of individual nerve cells. The consequence of this for neurobiological analysis is that the activity of a very large number of nerve cells has to be taken into consideration for understanding the brain. For experimental or apparatus-related reasons, therefore, traditional techniques for deriving neural activity encounter their limits. By way of example, it is no longer possible to detect electrical signals of a nerve cell by penetrating into individual cells using glass microelectrodes in the case of large cell assemblages having ten thousand or even millions of neurons, even in in-vitro experiments.

The prior art discloses methods for detecting the electrical potential of a cell or of a cell assemblage by means of sensors non-invasively, that is to say clearly without penetrating into the nerve cell to be examined. Such a concept is described for example in Thomas, C A et al. (1972) "A miniature microelectrode array to monitor the bioelectric activity of cultured cells" Exp. Cell. Res. 74:61–66. In accordance with this concept, a multiplicity of sensors can be operated simultaneously in time in order to record the activity of a neurobiological substance. In this case, a metal contact made of an inert material such as, for example, gold or platinum is used as sensor electrode. In accordance with the prior art, glass is often used as a substrate since it is optically transmissive and therefore enables the experimental arrangement to be monitored by means of a transmitted light microscope. However, the use of glass as a substrate for a sensor array has the disadvantage that the structure dimensions that can be achieved are not small enough, and that a sufficiently high spatial resolution of the activity of nerve cells cannot therefore be achieved.

A sensor arrangement having metallic electrodes is often referred to as a multi-electrode array (MEA).

A multi-electrode array has a known and often constant distance between adjacent sensor electrodes of the array, thus enabling neurobiologists to produce a so-called "map" of neural activity. In this case, it is possible to use biological samples such as brain samples, for example, in which the interlinking of the neurons is not altered by the preparation. In principle, a multi-electrode array has the advantage that the number of recording electrodes can be chosen to be sufficiently high, so that statistical properties of nerve cells can be detected for example in the case of cells that are similar to one another but are not interlinked with one another.

The function of a nerve cell is of interest for practical applications as a biochemical-electrical signal converter. The activity of neural cells is selectively influenced by specific substances, the fact that many of such substances are water-soluble being advantageous. Molecules that influence the activity of a neuron include, in particular, neurotransmitters, which are the subject of many pharmacological investigations. In particular, multi-electrode arrays with nerve cells, in particular from a rat brain, cultivated thereon have become ideal experimental objects for the development of pharmaceuticals. Advantages reside in the good experimental handling and in promising perspectives for long-term studies. The two-dimensional structure of a pharma-sensor comprising nerve cells and a sensor arrangement is essential for such an application.

The detection of toxic substances is another application of a coupled nerve cell/sensor system. Biosensors are distinguished by a high degree of specificity. Nerve cells, for example, are sensitive predominantly to those substances which are relevant to their metabolism. Therefore, an important area of use of biosensors is environmental monitoring, that is to say the detection of environmental parameters, in particular of toxic substances. However, in military and security fields, too, biosensors are capable of use on the basis of the aspect described. Such a concept is described for example in Gross, G W et al. (1995) "The use of neuronal networks on multielectrode arrays as biosensors" Biosensor&Bioelectronics 10:553–567.

However, it must be emphasized that the field of use of biosensors, in particular of the circuit arrangement according to the invention, of the sensor array according to the invention and of the biosensor array according to the invention, is not restricted to applications with nerve cells.

In the fields of use described or in other fields of use, the following requirements have to be made of sensor arrangements: a sufficient number of sensors are to be able to be operated simultaneously in order to make it possible to obtain a snapshot of the potential conditions on the active surface of the sensor arrangement. Furthermore, the distance between sensor elements or the spatial extent of a sensor element is to be chosen to be sufficiently small (typically 10·m to a few 10·m) in order to obtain a sufficiently good spatial resolution. A further important requirement made of such sensors is that the output signals of two arbitrary sensors of a multi-electrode array, given identical input signals, must likewise be identical. This means, in particular, that static differences in the output signals of the sensor elements (offset), which may be based for example on process fluctuations during the manufacture of the sensor elements, are not permitted to occur.

Solution approaches for forming sensors having the desired properties are, on the one hand, sensor arrangements having so-called IGFETs (Insulated Gate Field-effect Transistors) and, on the other hand, the multi-electrode arrays (MEA) already discussed.

In terms of its basic principle, such a FET is constructed similarly to a metal-insulator-semiconductor field-effect transistor (MISFET). It differs from a conventional MISFET by the fact that the conductivity of the channel region of the transistor is not controlled by means of a metal electrode, but rather by means of electrical or electrochemical processes within an electrolyte above the dielectric, it also optionally being possible for the dielectric to take up charges from the electrolyte. In other words, electrically charged particles to be detected (for example ions passing through the ion channels of nerve cells), via the electrolyte, are in contact with a dielectric layer at the surface of the dielectric, as a result of which a purely capacitive coupling is effected between the electrically charged particles to be detected and the channel region of the FET or else between the electrically charged particles to be detected and the gate electrode of the FET arranged below the dielectric layer of the FET. In other words, the dielectric layer acts like the dielectric of a capacitor which is formed between the electrically charged ions and directly the channel region of the FET or between the electrically charged ions of the gate electrode of the FET, in which case, by means of this capacitive coupling (without resistive components) of the charged particles at the surface of the FET sensor, the conductivity of the FET is altered on account of a sensor event, so that the value of the current flow between source and drain terminals of the FET is a measure of the sensor event. A direct ohmic contact, that is to say a direct penetration of the particles at an electrically conductive region of the FET, is not possible. The coupling is thus purely capacitive coupling.

An alternative solution concept for providing sensor arrangements which meet the abovementioned requirements is multi-electrode arrays. (MEAs). Multi-electrode arrays have an electrically conductive surface, usually a metal electrode, in direct operative contact with the electrically charged particles that initiate a sensor event. In order words, in multi-electrode arrays, the electrically charged particles are in direct operative contact with the surface of an electrode, so that the coupling between the particles to be detected and a sensor electrode is at least partly of resistive type. Although, in multi-electrode arrays, the coupling between the particles to be detected and the electrode may also have capacitive components (so-called Helmholtz layers, that is to say layers of particles having alternately positive and negative charges, may form at the surface of an electrode), the resistive components are nonetheless important. In multi-electrode arrays, therefore, the charge state of a node directly below the metal electrode is directly altered by particles to be detected.

In the case of multi-electrode arrays, it is possible, in turn, to distinguish between two concepts: optically and electrical drivable MEAs.

When using optically addressable multi-electrode arrays, metal electrodes of a multi-electrode array are arranged in matrix form. Dimensions of optically addressable multi-electrode arrays known from the prior art typically have 60 rows and 60 columns, the number of sensor elements resulting from the product of the rows with the columns. The electrodes of a column are in each case connected via a photoresistor to a common column line. A position within the sensor array is selected for example by using a laser to put the photoresistor associated with this position into an electrically conductive state by means of a light pulse. However, this concept has the disadvantage that in each case only one sensor array can be selected at one point in time. Furthermore, optical MEAs have the disadvantage that they have expensive and complicated components. Moreover, on account of the use of macroscopic components, such as a laser arrangement, for example, the construction of such sensor arrangements is often high, which counteracts a miniaturization that is striven for. Since optical MEAs in accordance with the prior art are predominantly formed on the basis of a glass substrate, for example the use of active switching or amplifier units, for example of preamplifiers directly below the electrode, is technologically not possible.

Moreover, in the case of the glass substrate technology, a sufficiently small dimensioning of the sensor elements and a sufficiently small distance between the sensor elements are not possible, so that both the temporal and the spatial resolution of the sensor elements require improvement.

One example of an electrically addressable MEA known from the prior art is shown in FIG. 1. The electrically addressable MEA 100 shown therein is formed on a glass substrate 101. By means of a boundary wall 102, an active sensor region 103 is formed in the central region of the electrically addressable MEA 100. A multiplicity of sensor arrays 104 are arranged essentially in matrix form in the active sensor region 103, the sensor arrays 104 being set up in such a way that they can detect a sensor event of an object to be examined that is arranged above them, for example of a nerve cell applied thereto. The electrical signals are conducted away via electrical leads 105 to contact areas 106 in the edge region of the electrically addressable MEA 100. The space requirement for the electrical leads 105 is very high. As a result, the maximum number of sensor arrays 104 that can be achieved is greatly restricted. The present technological limit of known MEAs is 64 sensor arrays. In addition to the severely restricted number of maximum sensor arrays 104 that can be achieved, on account of the separate electrical contact-connection of each individual sensor array 104 by means of electrical leads 105, a sufficiently good spatial resolution cannot be achieved. Furthermore, evaluation of the signals provided at the contact areas 106 requires complicated external evaluation electronics (not shown in FIG. 1), which increase the space requirement of the electrically adjustable multi-electrode array 100. Furthermore, a significant disadvantage of the electrically addressable MEAs 100 known from the prior art can be seen in the fact that the requirement that the output signals of two different sensors of an MEA 100, given identical input signals, are likewise identical is often not fulfilled. This is due, inter alia, to fluctuations in the process technology during the formation of the individual sensor arrays 104 and has the consequence that the detection sensitivity and the reliability of the sensor signals obtained require improvement. In other words different sensor arrays 104 of an electrically addressable MEA 100 have fluctuations with regard to the value of one or more physical parameters of the sensor elements 104, for example as a consequence of fluctuating process conditions during the production thereof, with the result that an unambiguous assignment of an electrical output signal to a sensor signal at an associated sensor array 104 is not possible.

Furthermore, Berdondini, L et al. "High-Density MEA for Electrophysiological Activity Imaging of Neuronal Networks" Proc. ICECS 2001, 1239–1242, September 2001, discloses an all-electronic multi-electrode array with electronic position selection, but this array likewise does not meet the aforementioned requirement that, in the case of different sensor arrays, an unambiguous output signal is to be assigned to a defined input signal.

DE 43 20 881 A1 discloses a combination of a heated lambda probe with a jumplike or binary sensor characteristic with a further heated lambda probe for determining the lambda value in a gas mixture, the output signal of one lambda probe serving to calibrate the other lambda probe.

SUMMARY OF THE INVENTION

The invention is based on the problem of providing an electronic multi-electrode array in which, even in the event of an alteration or a deviation of the value of a physical parameter of a sensor element from a reference value, i.e. a value of the physical parameter that occurs under normal, preferably predetermined, process conditions, a sensor signal generated by the sensor element is independent of the alteration of the value.

The invention is achieved by means of a circuit arrangement, a sensor array and a biosensor array having the features in accordance with the independent patent claims.

The circuit arrangement according to the invention has a substrate, a sensor element formed in or on a surface region of the substrate with a physical parameter, which can be coupled to a substance to be examined, the type of coupling having a resistive component, a calibration device formed in or on the substrate, said calibration device being set up in such a way that it can be used to at least partly compensate for an alteration of the value of the physical parameter of the sensor element.

Furthermore, the invention provides a sensor array having a plurality of circuit arrangements having the abovementioned features, said circuit arrangements being arranged essentially in matrix form in crossover regions of row and column lines and being connected up to the row and column lines.

Furthermore, a biosensor array having a sensor array having the abovementioned features is provided.

The circuit arrangement according to the invention has the feature, in particular, that the components of the circuit arrangement, in particular the sensor elements and the calibration device, can be integrated into a substrate, preferably a semiconductor-technological substrate. This brings about a miniaturization of the arrangement, thereby improving the spatial resolution of a sensor array based on the circuit arrangement according to the invention. Furthermore, it is possible to use customary and thus mature processes of semiconductor technology according to the invention in order to form the circuit arrangement. The circuit arrangement can thus be produced in a manner that is not very complicated. One important advantage of the circuit arrangement according to the invention over the prior art is that, on account of the compensation of an alteration of the value of the physical parameter of the sensor element by means of the calibration device formed in and/or on the substrate, an unambiguous assignment of a sensor element to a sensor event effected at the associated sensor element is possible even if the respective physical parameter or a plurality of such physical parameters have a different value between different sensor elements, for example on account of process fluctuations. By way of example, as described below, the sensor element may have a measuring transistor whose threshold voltage or other parameters vary around a mean or reference value on account of process fluctuations during the formation of the sensor elements. Sensor elements having a different value of said physical parameter yield different sensor signals for the same sensor event in accordance with the prior art. The calibration device according to the invention is set up in such a way that this disadvantageous effect is precisely avoided by at least partly compensating for an alteration of the value of the physical parameter of the sensor element. As a result, the measurement accuracy or the reproducibility of a sensor array based on the circuit arrangement according to the invention is increased, and an overly high exactness is dispensable in the production of the sensor element of the sensor array.

In the context of this description, a physical parameter is understood to be any desired parameter of the sensor element, for example the threshold voltage of a measuring transistor of the sensor element, which parameter, in the case of a specific sensor event, influences the resulting sensor signal, this influencing being at least partly avoided by means of the calibration device.

The sensor element of the circuit arrangement preferably has an electrically conductive sensor electrode that can be coupled to the substance to be examined.

The sensor element may furthermore have a measuring transistor, the gate terminal of which is coupled to the electrically conductive sensor electrode.

The measuring transistor is thus preferably a field-effect transistor, in particular a MOSFET. However, it is possible as an alternative to use a bipolar transistor as the measuring transistor of the sensor element, the base terminal of the bipolar transistor forming the functionality of the gate terminal of a field-effect transistor, and the emitter and collector terminals of the bipolar transistor forming the functionality of the source/drain terminals of the field-effect transistor. The use of a measuring transistor as an active element of the sensor element means that a highly sensitive component that is not very complicated and has small structural dimensioning is used.

Furthermore, the circuit arrangement according to the invention may have a device for detecting an electrical parameter that characterizes an effected sensor event, which device can be coupled to a first source/drain terminal of the measuring transistor. Said device may be, in particular, a voltmeter for detecting an electrical voltage or an ammeter for detecting an electric current; however, it is also possible to detect a different electrical parameter such as, for example, an electrical resistance or a frequency. Clearly, the charge state of the gate terminal of the measuring transistor is influenced on account of a sensor event, thereby altering an electric current between the two source/drain terminals of the measuring transistor. An electrical signal corresponding to this current flow, either the current flow itself or an electrical voltage associated therewith or another electrical signal, is then detected by means of the device for detecting this electrical parameter.

Furthermore, the calibration device may be set up in such a way that it can be used to control the electrical potential applied to the first or a second source/drain terminal of the measuring transistor in such a way that it can set a sensor signal of the sensor element, said sensor signal being brought about by a sensor event, to a value which is independent of the value of the physical parameter of the sensor element.

Clearly, on account of the functionality of the calibration device, one of the two source/drain terminals of the measuring transistor is brought to an electrical potential such that an alteration of the value of the physical parameter of said sensor element is thereby at least partly compensated for and different sensor elements having different values of this physical parameter, given an identical sensor event, generate an identical or essentially identical sensor signal.

The calibration is thus effected via one of the two source/drain terminals of the measuring transistor. As an alternative, the calibration may be effected via the substrate terminal (bulk terminal) of the measuring transistor. In this case, each measuring transistor acquires a dedicated well that can be contact-connected separately and whose potential can be set for example by means of a source follower, thereby influencing the transfer properties of the measuring transistor formed therein or thereon. In other words, all the electrical nodes of a MOSFET (first source/drain terminal, second source/drain terminal, bulk terminal) except for the gate terminal may serve to be brought to a potential such that, as a result of this, the associated sensor element is calibrated or the alteration of the value of the physical parameter of the sensor element is at least partly compensated for.

In particular, the calibration device of the circuit arrangement may be set up in such a way that it can be used to control the electrical potential present at the first source/drain terminal of the measuring transistor.

This is realized in particular in the case of a circuit arrangement in which a first electrical reference potential, for example the ground potential, can be applied to the second source/drain terminal of the measuring transistor, and in which the calibration device has a calibration transistor having a first and a second source/drain terminal, which source/drain terminals are connected between the first source/drain terminal of the measuring transistor and the device for detecting an electrical parameter, and it is possible to apply to the gate terminal thereof an electrical signal such that the electrical potential which can be applied to the first source/drain terminal of the measuring transistor can be set in such a way that the alteration of the value of the physical parameter of the sensor element can at least partly be compensated for.

In other words, in accordance with this refinement, the calibration transistor is operated as a gate-controlled source follower, the second source/drain terminal of the calibration transistor being coupled to the first source/drain terminal of the measuring transistor, and a node between the second source/drain terminal of the calibration transistor and the first source/drain terminal of the measuring transistor being brought, via the gate terminal of the calibration transistor, to an electrical potential such that the alteration of the value of the physical parameter of the sensor element is thereby at least partly compensated for.

As an alternative, the calibration device of the circuit arrangement may be set up in such a way that it can be used to control the electrical potential present at the second source/drain terminal of the measuring transistor.

This may be realized in that the first source/drain terminal of the measuring transistor is coupled to the device for detecting an electrical parameter, and in that the calibration device has a calibration transistor having a first source/drain terminal, which is coupled to the second source/drain terminal of the measuring transistor, and a second source/drain terminal, to which a second electrical reference potential can be applied, and to the gate terminal of which it is possible to apply an electrical signal such that the electrical potential which can be applied to the second source/drain terminal of the measuring transistor can be set in such a way that the alteration of the value of the physical parameter of the sensor element can at least partly be compensated for.

In this case, the calibration is realized by means of a source negative feedback of the calibration transistor with respect to the measuring transistor, a charge remaining on the gate terminal of the calibration transistor. Clearly, the calibration transistor is operated as a controllable resistor in this case, the resistor being set to a value which has the effect of at least partly compensating for an alteration of the value of the physical parameter of the sensor element.

As an alternative, the calibration device of the circuit arrangement may have a calibration transistor, a first constant-current source, which is coupled to respective second source/drain terminals of the measuring and calibration transistors that are connected in parallel with one another, for the provision of a predeterminable electrical current intensity, and a current mirror circuit, which is coupled to respective first source/drain terminals of the measuring and calibration transistors that are connected in parallel with one another, and which is connected up in such a way that it can be used to set, for the purpose of at least partly compensating for the alteration of the value of the physical parameter, the electrical potential at the gate terminal of the calibration transistor in such a way that, in the absence of a sensor event, the current flow between the two source/drain terminals of the measuring transistor and the current flow between the two source/drain terminals of the calibration transistor are essentially identical.

In accordance with this refinement of the circuit device according to the invention, a measuring transistor and a calibration transistor are operated in two current branches that are connected in parallel with one another, and, using the functionality and a suitable interconnection of the current mirror circuit, it is ensured that an essentially identical current flows in the two current branches in the absence of a sensor event. An identical current in the two parallel-connected branches with measuring and calibration transistors brings about a setting of the potentials at the nodes of the measuring and calibration transistors such that, even in the event of a deviation of the value of the physical parameter of the measuring and calibration transistors in the case of a sensor event, a sensor current independent of the value of the physical parameters flows.

As an alternative, in the circuit arrangement according to the invention, a third electrical potential may be applied to the first source/drain terminal of the measuring transistor and the calibration device may have a calibration transistor having a first and a second source/drain terminal, a second constant-current source, which is coupled to the respective second source/drain terminals of the measuring and calibration transistors that are connected in parallel with one another, for the provision of a predeterminable electrical current intensity, and a third constant-current source, which can be coupled to the first source/drain terminal of the calibration transistor, for the provision of a further predeterminable electrical current intensity, which third constant-current source is connected up in such a way that it can be used to set, for the purpose of at least partly compensating for the alteration of the value of the physical parameter, the potentials that can be applied to the terminals of the transistors in such a way that, in the absence of a sensor event, the current flows between the two source/drain terminals of the measuring transistor, on the one hand, and between the two source/drain terminals of the calibration transistor, on the other hand, are identical in magnitude.

In accordance with an alternative realization, the calibration device in the circuit arrangement is set up in such a way that it can be used to convert a sensor signal of the sensor element, said sensor signal being brought about by a sensor event, using the principle of correlated double sampling (CDS) to a value which is independent of the value of the physical parameter of the sensor element.

In particular, in accordance with the CDS principle, in the circuit arrangement, a fourth electrical reference potential may be applied to a second source/drain terminal of the measuring transistor, and the calibration device may have an electrical subtraction device having two inputs and an output, which output can be coupled to the device for detecting an electrical parameter, which first input is coupled to the first source/drain terminal of the measuring transistor, and which electrical subtraction device is set up in such a way that the difference between two electrical signals applied to the two inputs can be provided at its output. Furthermore, the calibration device may have a sample-and-hold element connected between the first source/drain terminal of the measuring transistor and the second input of the electrical subtraction device. The calibration device is set up in such a way that in a first operating state, a sensor signal dependent on the physical parameter of the sensor element can be impressed into the sample-and-hold element and can be provided to the second input of the electrical subtraction device. In a second operating state, a signal which is characteristic of the physical parameter of the sensor element can be provided to the first input of the electrical subtraction device. According to the second operating state, a sensor signal independent of the value of the physical parameter of the sensor element can be provided at the output of the electrical subtraction device, as a result of which the alteration of the value of the physical parameter is at least partly compensated for.

In other words, first of all, in a first step, a sensor event is detected in the sensor element and a sensor signal is provided to the sample-and-hold element and stored therein. Said sensor signal is dependent on the alteration of the value of the physical parameter of the first sensor element, and may furthermore be dependent on physical parameters of further components, for example of an amplifier for amplifying the sensor signal. The signal stored in the sample-and-hold element is therefore different for different sensor elements having different values of the physical parameter. In the second operating state, a sensor signal is not detected, so that an auxiliary signal which is provided to the first input of the electrical subtraction device is independent of the sensor event, and depends on the value of the physical parameter or on the alteration of the value of the physical parameter. The electronic subtraction device is set up in such a way that it can form the difference between the signal dependent on the value of the physical parameter at the first input and the sensor signal provided at the second input including a partial signal dependent on the physical parameter, so that a sensor signal that is essentially independent of the value of the physical parameter can be provided at the output of the electronic subtraction device.

Clearly, the calibration device in accordance with the refinements described has components (in particular transistors and capacitances, for example formed by the gate capacitance of a transistor) which can be used to store specific values of the physical parameter during a calibration phase for a respective sensor element, which, in combination with a suitable interconnection with the remaining components of the circuit arrangement or of the sensor array, has the effect that all the sensor elements have an identical transfer characteristic independently of the respective alteration of the value of the physical parameter, or that the offset values thereof are at least partly adjusted.

In particular, the electronic parameter of the circuit arrangement may be an electrical voltage or an electric current.

Generally, a resistively coupled sensor element will have, as sensor signal, an electric current between the two source/drain terminals of the measuring transistor that is preferably contained therein. Said electric current may for example be detected directly as a sensor event. As an alternative, which may be less complicated in specific applications, an electrical voltage dependent on the electric current described may be used as the electrical parameter to be detected. In order to convert an electric sensor current into an electrical sensor voltage, it is possible, for example, to use a current-voltage converter, for example a resistor across which a sensor voltage is dropped on account of the sensor current.

The sensor electrode of the circuit arrangement according to the invention preferably has one or a combination of the materials titanium, titanium nitride, gold and platinum. These materials all have the property of being readily electrically conductive and chemically inert. The low sensitivity toward possibly chemically aggressive electrolytes in operative contact with the sensor electrode and the compatibility of the materials described with frequently sensitive biological substances have the effect that these materials are well suited as material for the sensor electrode. In particular, a titanium sensor electrode covered with a thin titanium nitride layer is particular advantageous since titanium nitride in thin layers is a good electrical conductor, is chemically inert, is biocompatible and has a high active surface area. This sensor electrode is in contact with the electrolyte and serves to conduct away the signals, for example the cellular signals of nerve cells.

Furthermore, the circuit arrangement according to the invention may have at least one integrated amplifier element for amplifying a sensor signal.

Amplifying the often small electrical sensor signals increases the sensitivity. By effecting the amplification in the vicinity of the sensor signal, that is to say after a short transmission path of the electrical signal, the signal-to-noise ratio is increased. Examples of suitable amplifiers are voltage amplifiers or transconductance amplifiers.

In accordance with a preferred development, the circuit arrangement has a switching device set up in such a way that it can be used optionally to couple the sensor element to a fifth electrical reference potential or to decouple it from the latter, in order to protect the sensor element from damage and/or in order to apply a defined electrical potential to the sensor element.

Such a switching device may bring about a connectable or disconnectable electrical coupling of the input of the measuring transistor to an electrical voltage prescribed internally in the circuit. This is advantageous in particular in an operating state in which a sensor array based on the circuit arrangement according to the invention is filled with an electrolyte, since electrical flashovers could occur at the input of the measuring transistor during this operation if the input is at very high impedance, for example if the input is coupled to the gate terminal of a MOS transistor. By virtue of a predeterminable electrical reference potential being applied to the input of the measuring transistor by means of the switching device, the sensitive measuring transistor, formed as an integrated component, is protected from electrical flashovers. Furthermore, during the production of a multi-electrode array, a process-dictated electrical charging (so-called antenna effects) may occur at the input of a measuring transistor if the input is embodied as a gate terminal of a MOS transistor and this terminal has no further connection to another circuit node. The measuring transistor is protected from such disadvantageous effects if the gate terminal of the measuring transistor is coupled to the electrical reference potential. Furthermore, it may be necessary for specific applications to connect at least a part of the gate terminals of the measuring transistors of the circuit arrangements of a sensor array to a reference potential, for example during a calibration phase.

The substrate of the sensor arrangement is preferably a silicon substrate in particular a silicon wafer or a silicon chip. In this case, the advantages and mature customary processes of silicon microelectronics can be used to produce the sensor arrangement according to the invention.

The type of coupling between the sensor element and the liquid to be examined may additionally have a capacitive component.

Refinements of the sensor array according to the invention, which has circuit arrangements according to the invention, are described below. Refinements of the circuit arrangement also apply to the sensor array having circuit arrangements.

By virtue of the fact that the invention provides a sensor array having a plurality of circuit arrangements, said circuit arrangements being arranged essentially in matrix form in crossover regions of row and column lines and being connected up to the row and column lines, it is possible to achieve a high integration density of sensor elements and a high degree of miniaturization, as a result of which the spatial resolution of the sensor array is high.

Preferably, in the sensor array, at least a part of the circuit arrangements have a selection element—coupled to the respectively associated row line and/or column line—for selection of the respective sensor arrangement in order to detect a sensor signal of the sensor element of the selected circuit arrangement and/or in order, in the case of the selected circuit arrangement, at least partly to compensate for the alteration of the value of the physical parameter and/or in order to apply the fifth electrical potential to the sensor element of the selected circuit arrangement.

Such a circuit enables the selection of a sensor element or of a circuit arrangement of the sensor array and is set up in such a way as to provide signals for driving selection elements for example at an end section of row and column lines.

It is also possible to provide a circuit having a multiplexer for progressively selecting sensor elements, which circuit can be controlled for example by means of a control signal.

In accordance with a preferred development of the sensor array according to the invention, at least a part of the circuit arrangements assigned to a respective row and/or column line have a common device for detecting an electrical parameter that characterizes an effected sensor event, a common constant-current source, a common switching device, a common reference potential, a common current-voltage converter, a common analog-digital converter, a common current mirror, a common differential stage, a common subtraction device, a common sample-and-hold element, and/or a common amplifier.

By virtue of the fact that a component assigned to a respective circuit arrangement in accordance with the above description is not assigned to every individual circuit arrangement, but rather to a part or all of the circuit arrangements of a row or a column, components are saved, thereby reducing the space requirements and the production outlay. In other words, it is possible, for example, to provide a common amplifier at the end section of a column line, so that not every individual circuit arrangement of the column line has to have a separate amplifier. In particular, it must be emphasized that an amplified analog signal derived from a sensor element can already be converted into a digital quantity on-chip (by means of an analog-to-digital converter), as a result of which the robustness in respect of errors is increased and the detection sensitivity is improved. Moreover, the sensor array may have circuits or circuit components which, with the components of the individual circuit arrangements, form regulating circuits which are activated during the calibration phase and serve to provide calibration quantities that are to be stored within the circuit arrangements (for example at suitable nodes or terminals of transistors).

Furthermore, in the sensor array, at least a part of the row and/or column lines in each case have a device for detecting an electrical parameter that characterizes an effected sensor event, the sensor array being set up in such a way that the device for detecting an electrical parameter that is assigned to a respective row or column line can detect either a sensor signal of precisely one sensor arrangement of the respective row or column line, or a sum of sensor signals of at least a portion of the sensor arrangement in the respective row or column line. In other words, it is optionally possible to detect, for example along a column line either the sensor signal of precisely one sensor element of the column line or of a portion of the sensor elements of the column line or of all the sensor elements of the column line. In the latter case, a summation current signal of the sensor element of a column line is detected and evaluated. It goes without saying that such detection of summation current signals is also possible along a row line.

At least a part of the column lines of the sensor array according to the invention may be coupled to a potential control device, which is set up in such a way that it holds the electrical potential of the associated column line at an essentially constant value. By virtue of the fact that the electrical potential of a column line can be held at an essentially constant value by means of a potential control device, an improved reproducibility and an increase in the measurement accuracy are achieved.

As discussed above, the invention also provides a biosensor array having a sensor array having the abovementioned features. In other words, the sensor array according to the invention can readily be used as a sensor for detecting such signals which originate from biological systems, such as nerve cells, for example, which are applied to the biosensor array or are grown thereon. On account of the high spatial resolution of the biosensor array, the biocompatibility of the materials used and the detection sensitivity of sensor elements of the biosensor array, the latter is ideal for biological applications.

BRIEF DESCRIPTION OF THE DRAWINGS

Exemplary embodiments of the invention are illustrated in the figures and are explained in more detail below. In the figures.

DETAILED DESCRIPTION OF THE PREFERRED MODE OF THE INVENTION

Figure 1:
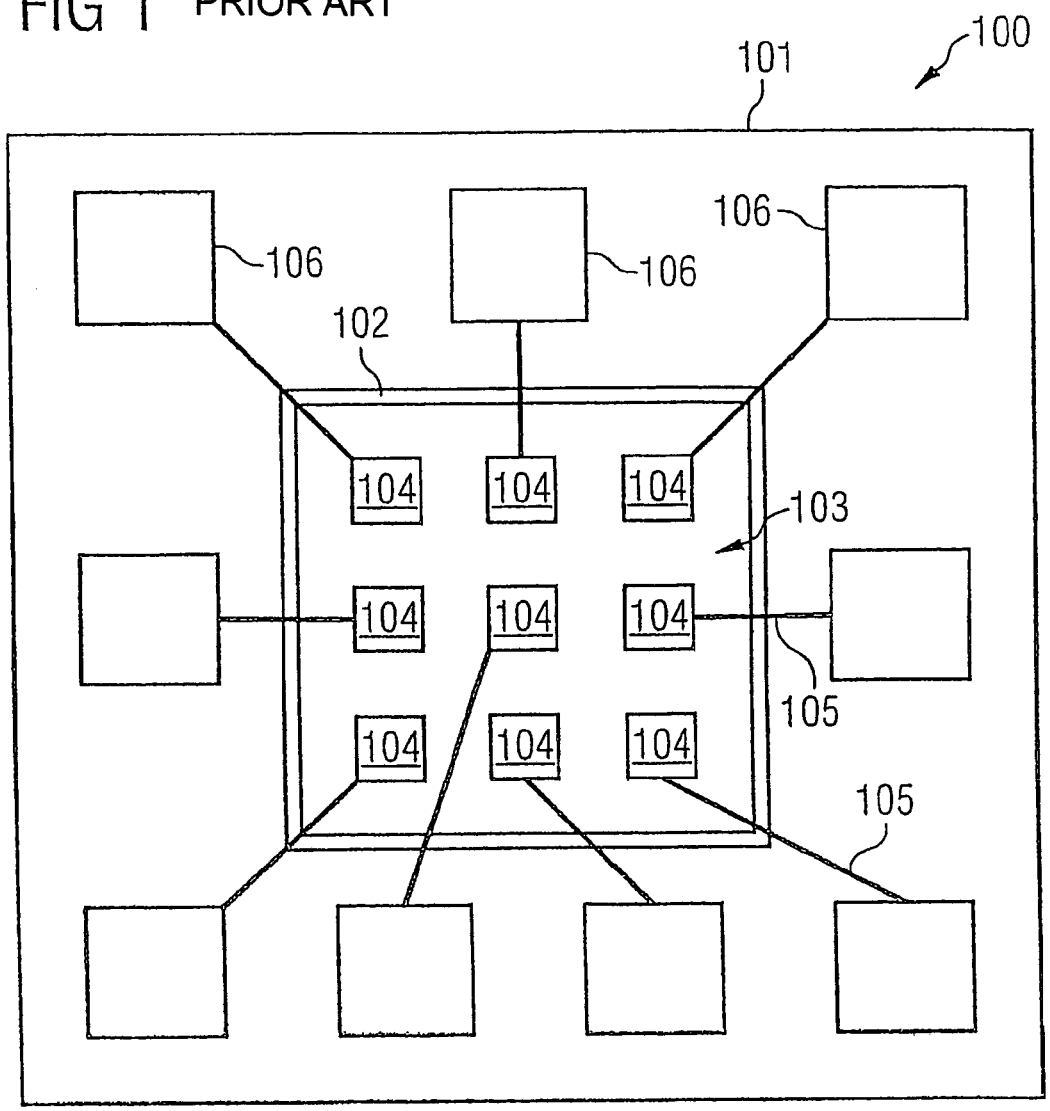
FIG. 1 shows an electrically addressable multi-electrode array in accordance with the prior art.

It should be noted that, in the exemplary embodiments of the sensor array according to the invention that are described below with reference to FIG. 2 to FIG. 19 many of the components described occur in different exemplary embodiments. Such components are in each case provided with the same reference numerals in different exemplary embodiments. Furthermore, the functionality of subcircuits of the different exemplary embodiments of the sensor array according to the invention is also identical in some instances, so that this functionality is not described in detail for every exemplary embodiment and, therefore, reference is made back to other exemplary embodiments.

Figure 2:
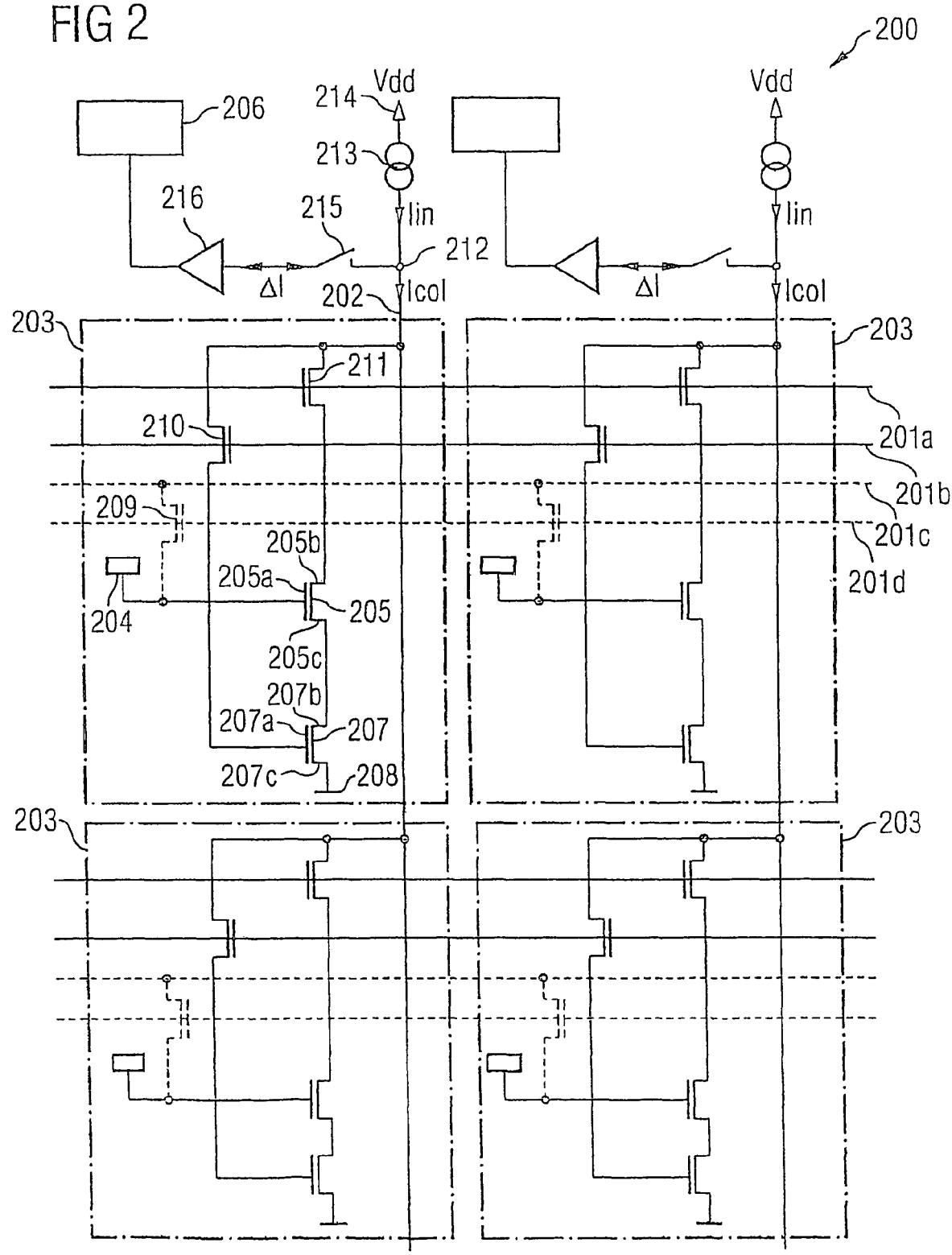
FIGS. 2 to 19 show sensor arrays in accordance with preferred exemplary embodiments of the invention.

FIG. 2 shows a sensor array 200 in accordance with a first preferred exemplary embodiment of the invention.

The sensor array 200 has a plurality of biosensor circuit arrangements 203 which are arranged in matrix form in crossover regions of row lines 201a, 201b, 201c, 201d and column lines 202 and are connected up to the row and column lines 201a, 201b, 201c, 201d, 202. FIG. 2 shows a total of four biosensor circuit arrangements 203, but these arrangements show only an extract from the matrix-type arrangement of biosensor circuit arrangements 203. Biosensor circuit arrangements 203 of a row are arranged in the horizontal direction in accordance with FIG. 2, and the biosensor circuit arrangements 203 of a column are arranged in the vertical direction in accordance with FIG. 2. In accordance with the exemplary embodiment shown in FIG. 2, each of the biosensor circuit arrangements 203 has the same internal interconnection, so that only the construction and the interconnection of a biosensor circuit arrangement 203 is described in more detail below.

Each biosensor circuit arrangement 203 has an electrically conductive sensor electrode 204 made of gold that is coupled to a substance to be examined, for example a nerve cell (not shown in the figures). Furthermore, the sensor element contained in the biosensor circuit arrangement 203 has a measuring transistor 205, the gate terminal 205a of which is coupled to the electrically conductive sensor electrode 204. The sensor element of the biosensor circuit arrangement 203 is formed by the sensor electrode 204 and the measuring transistor 205. The coupling of the sensor element to the substance to be examined (not shown in FIG. 2) has a resistive component, i.e. there is a direct electrical contact between electrically charged particles in the liquid to be examined and the gate terminal 205a of the measuring transistor 205, said gate terminal being coupled to the sensor electrode 204. Furthermore, FIG. 2 shows an ammeter 206 for detecting an electric current that characterizes an effected sensor event, which ammeter 206 can be coupled via a plurality of other components to the first source/drain terminal 205b of the measuring transistor 205. The biosensor circuit arrangements 203 are integrated into a silicon substrate (not shown). In particular, each of the biosensor circuit arrangements 203 has a calibration device which is formed in or on the substrate and is set up in such a way that it can be used to at least partly compensate for an alteration of the value of a physical parameter of the sensor element. In other words, each of the sensor elements 204 of the biosensor circuit arrangement 203 has a value of the physical parameter, namely the threshold voltage of the measuring transistor 205, which varies around a reference value in the different sensor elements. The calibration device, as is described below, is able to store an electrical charge as correction quantity at a node of the associated sensor element, so that all the measuring transistors 205 can clearly be operated at the same operation point, independently of the value of the actual physical parameter of the respective transistor. In the biosensor circuit arrangement 203, the calibration device is set up in such a way that it can be used to control the electrical potential present at a second source/drain terminal 205c of the measuring transistor 205. The first source/drain terminal 205b of the measuring transistor 205, as shown in FIG. 2, is coupled to the ammeter 206, and the calibration device has a calibration transistor 207 having a first source/drain terminal 207b, which is coupled to the second source/drain terminal 205c of the measuring transistor 205, and a second source/drain terminal 207c to which an electrical ground potential 208 is applied, and to the gate terminal 207a of which calibration transistor it is possible to apply an electrical signal such that the electrical potential that can be applied to the second source/drain terminal 205c of the measuring transistor 205 can be set in such a way that the alteration of the value of the threshold voltage (physical parameter) of the respective sensor element can be at least partly compensated for.

Furthermore, each biosensor circuit arrangement 203 has a first switching transistor 209, the source/drain terminals of which are connected between the gate terminal 205a of the measuring transistor 205 and the associated third row line 201c. Furthermore, the gate terminal of the first switching transistor 209 is coupled to the associated fourth row line 201d. The first switching transistor 209 and the third and fourth row lines 201c, 201d form a switching device which is set up in such a way that it can be used optionally to couple the assigned sensor element to an electrical reference potential applied to the third row line 201c or decouple it from said reference potential, in order to protect the associated sensor element from damage and/or in order to provide a defined electrical potential, namely the potential applied to the third row line 201c, to the associated sensor element. The electrical potential present on the third row line 201c is applied to the gate terminal 205a of the measuring transistor 205 when a corresponding switching signal by means of which the first switching transistor 209 is turned on is applied to the fourth row line 201c. The gate terminal 207a of the calibration transistor 207 is coupled to a source/drain terminal of a second switching transistor 210, the gate terminal of which is coupled to the associated second row line 201b. The first source/drain terminal 205b of the measuring transistor 205 is coupled to a source/drain terminal of a third switching transistor 211, the gate terminal of which is coupled to the associated first row line 201a. The respective other source/drain terminals of the second and third switching transistors 210, 211 are coupled to an associated column line 202. An electrical node 212 is arranged at the end section of each column line 202. The first electrical node 212 is coupled to a constant-current source 213, to which a supply voltage 214 is applied. Furthermore, the first electrical node 212 is coupled via a first switch 215 and a first amplifier 216 and to the ammeter 206. The first amplifier 216 serves to amplify a sensor signal.

The functionality of the sensor array 200 is described below. In the case of the sensor array 200 from FIG. 2, applying an electrical signal to the first row line 201a activates precisely one sensor arrangement 203 in each column line 202. The sensor signal—provided at an end section of the column line 202—of a sensor element of a biosensor circuit arrangement 203 contains a sensor current •I on which a bias current $I_{in}$ is superposed.

By means of the constant-current source 213, the current $I_{in}$ is fed into each column line 202, to be precise both during a calibration phase and during a measurement phase (see description below). A specific row of biosensor circuit arrangements 203 is selected by an electrical signal being applied to an associated first row line 201a, as a result of which the third switching transistor 211 is turned on.

In a calibration phase, the first switches 215 are open, so that the current $I_{in}$ is identical to the column current $I_{col}$ flowing in a column line 202. Furthermore, an electrical signal is applied to the second column lines 201b, so that the second switching transistor 210 coupled thereto is turned on. The current intensity $I_{col}$ then also flows between the respective source/drain terminals of the third switching transistor 211, of the measuring transistor 205 and of the calibration transistor 207.

If the calibration transistor 207 is operated in saturation, that is to say if the difference between the voltage between the gate terminal 205a and the second source/drain terminal 205c of the measuring transistor 205 and the threshold voltage of the measuring transistor 205 is less than the voltage between the two source/drain terminals 205b, 205c of the measuring transistor 205, then the following holds true to an approximation for the current flow IDS through the first source/drain terminal 205b of the measuring transistor 205:

$$I_{DS}=1/2 W/LK[V(E)-(V_t-\bullet V_t)-V_{12}]^2 \quad (1)$$

In this case, k is a technology-dependent constant, also called transistor constant, W/L is the ratio between width W and length L of the transistor, V(E) is the electrical voltage present at (or applied to) the sensor electrode 204, which voltage is identical to the electrical potential of the gate terminal 205a of the measuring transistor 25, $V_t$ is a mean or reference value of the threshold voltages of different measuring transistors 205 of the biosensor circuit arrangements 203 of the sensor array 200, $\bullet V_t$ is the individual deviation or alteration of the threshold voltage of a specific measuring transistor 205 of the sensor array 200 from the mean value $V_t$ (expressed generally: the alteration of the physical parameter), and $V_{12}$ is the common electrical voltage at the second source/drain terminal 205c of the measuring transistor 205 and at the first source/drain terminal 207b of the calibration transistor 207. Since the dependence of the current through the first source/drain terminal on the voltage between the two source/drain terminals is low in the case of a transistor having an operating point in the saturation region, this effect is negligible (cf. general transistor characteristic curve).

On account of the circuitry constraint $$I_{in}=I_{col}=I_D \quad (2)$$

resulting in the calibration phase (first switch 215 open) in the case of the interconnection in accordance with FIG. 2, in the case of a specific electrical voltage is established at the gate terminal 207a of the calibration transistor 207. Said voltage defines the conductivity state of the channel region of the calibration transistor 207, which calibration transistor 207 is therefore clearly operated as a controllable resistor and consequently brings about a source negative feedback of the measuring transistor 205. Since the circuitry configuration of FIG. 2 constitutes a closed regulating circuit, the voltage drop $V_{22}$ produced across the calibration transistor 207 is precisely the voltage drop for which equations (1) and (2) are simultaneously fulfilled. In particular, this means that an individual value $V_{12}$ is obtained for each biosensor circuit arrangement 203, which individual value depends on the alteration of the threshold voltage of the associated measuring transistor 205:

$$V_{12nm}=\bullet V_{nm}+\text{const.} \quad (3)$$

In this case, n designates the ordinal number of the row and m the ordinal number of the column of the respective biosensor circuit arrangement 203 in the matrix-type arrangement of biosensor circuit arrangements 203.

If the electrical charge states described have been established at the terminals of the measuring transistor 205 and of the calibration transistor 207, the electrical signal previously applied to the associated second row line 201b is switched off, so that the second switching transistor 210 is no longer in the on state. The quantity of charge which was applied during the calibration phase remains on the capacitance of the gate terminal 207a of the calibration transistor 207, that is to say that the gate voltage of the calibration transistor 207 remains unchanged and the pixel is calibrated.

The regulating and calibrating mechanism described also functions if not just a single physical parameter, the threshold voltage of the measuring transistor 205 in the exemplary embodiment described, is subjected to fluctuations, but also when a plurality (for example in addition the factor k in equation (1) or further parameters in a more detailed description of the transistor) of physical parameters have a value that deviates from a mean value, for example on account of process fluctuations. Furthermore, it should be noted that the regulating and calibrating mechanism described likewise functions if, something which has been disregarded on account of the saturation operation of the measuring transistor 205, the dependence of the current flow between the source/drain terminals 205b, 205c of the measuring transistor 205 on the voltage between the two source/drain terminals 205b, 206c of the measuring transistor 205 is taken into account, for instance in a scenario in which said dependence is greater than during the operation of the transistor in saturation.

In a measurement phase, the first switch 215 is closed. Changes in the potential of the associated sensor electrode 204 lead to a change in the current through the first source/drain terminal 205b of the measuring transistor 205 and thus to a change in the column current $I_{col}$. The difference between $I_{in}$ and $I_{col}$ flows via the closed first switch 215 into the input of the first amplifier 216. The first amplifier 216 may be a current amplifier, or it may convert the input current into an output voltage and therefore function as a current-voltage converter.

If should be taken into consideration that the sensor current detected by the ammeter 206 after calibration and measurement phase have been effected is independent of the sensor element formed from sensor electrode 204 and measuring transistor 205 which is subjected to a variation of the threshold voltage or another physical parameter, so that it is ensured on account of the calibration that each of the biosensor circuit arrangements 203 shown in FIG. 2 bring about a specific sensor current at the ammeter 206 in the case of a specific sensor signal.

A second preferred exemplary embodiment of the sensor array according to the invention is described below with reference to FIG. 3.

Figure 3:
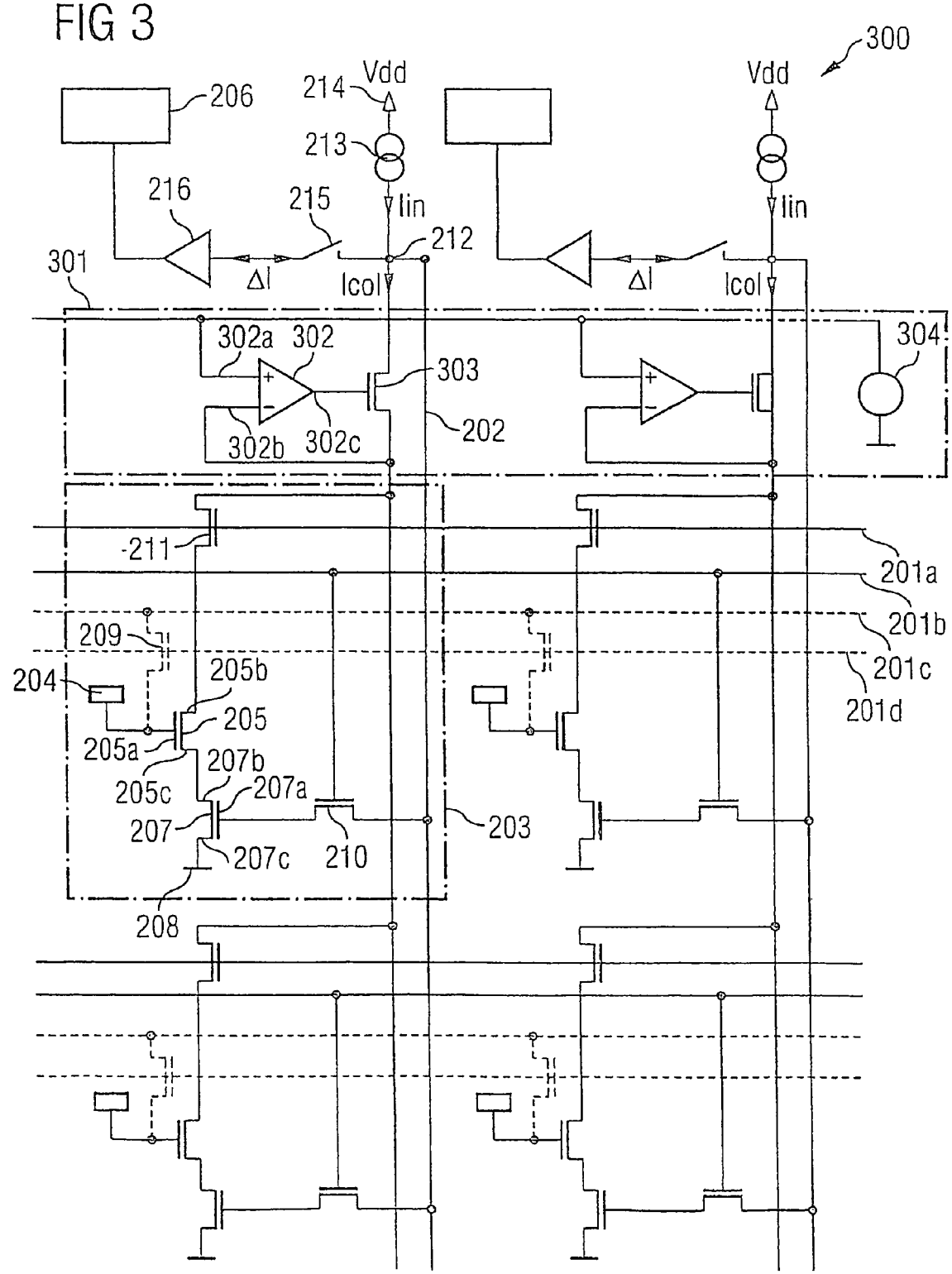

The sensor array 300 shown in FIG. 3 differs from the sensor array 200 shown in FIG. 2 by the fact that the column lines 202 are coupled to a potential control device 301, which potential control device 301 is set up in such a way that it holds the electrical potential of the associated column line 302 at an essentially constant value.

The potential control device 301 shown in FIG. 3 has an operational amplifier 302 having a non-inverting input 302a and an inverting input 302b and an output 302c and has a fourth switching transistor 303, the gate terminal of which is coupled to the output 302c of the operational amplifier 302. One source/drain terminal of the fourth switching transistor 303 is coupled to the first electrical node 212, and the other source/drain terminal of the fourth switching transistor 303 is coupled both to the inverting input 302b of the operational amplifier 302 and to a source/drain terminal of the third switching transistor 211. Furthermore, the potential control device 301 has a first voltage source 304, by means of which the non-inverting input 302a of the operational amplifier 302 can be brought to a predeterminable electrical potential.

In the case of the sensor array 300 from FIG. 3, the electrical potential of the column lines 202 and therefore the electrical potential at the first source/drain terminal 205b of the measuring transistor 205 can be held at a constant potential both in the calibration phase and in the measurement phase by means of the control circuit constructed by means of the operational amplifier 302 and the fourth switching transistor 303. As a result, the accuracy of the calibration can be increased further. Different potentials of the first source/drain terminal 205b during the calibration phase and during the measurement phase of the measuring transistor 205 may lead to small undesirable differential currents •I, which may bring about a parasitic input signal at the first amplifier 216. This problem is avoided in the case of the exemplary embodiment of the sensor array 300 as shown in FIG. 3.

A third preferred exemplary embodiment of the sensor array according to the invention is described below with reference to FIG. 4.

The sensor array 400 shown in FIG. 4 has the same components as the sensor array 200 described with reference to FIG. 2. However, the interconnection within the biosensor circuit arrangements of the sensor array 400 is different than in the case of the sensor array 200. Therefore, the interconnection and the functionality of the biosensor circuit arrangement 401 are described below.

In the case of the sensor array 400, the sensor electrode 204 is coupled to the gate terminal 205a of the measuring transistor 205. The second source/drain terminal 205c of the measuring transistor 205 is coupled to the ground potential 208. The first source/drain terminal 205b of the measuring transistor 205 is coupled to the second source/drain terminal 207c of the calibration transistor 207. The first source/drain terminal 207b of the calibration transistor 207 is coupled to a source/drain terminal of the third switching transistor 211, and the gate terminal 207a of the calibration transistor 207 is coupled to a source/drain terminal of the second calibration transistor 210. The other source/drain terminal of the second switching transistor 210 is coupled to the first electrical node 212, in the same way as the other source/drain terminal of the third switching transistor 211.

In the case of the biosensor circuit arrangement 401, a ground potential 208 is applied to the second source/drain terminal 205c of the measuring transistor 205, and the two source/drain terminals 207b, 207c of the calibration transistor 207 of the calibration device are connected between the first source/drain terminal 205b of the measuring transistor 205 and (via a plurality of other components) the ammeter 206, and it is possible to apply to the gate terminal 207a of the calibration transistor 207 an electrical signal such that the electrical potential which can be applied to the first source/drain terminal 205b of the measuring transistor 205 can be set in such a way that the alteration of the value of the physical parameter namely the threshold voltage of the measuring transistor 205 of the sensor element, can be at least partly compensated for.

Figure 4:
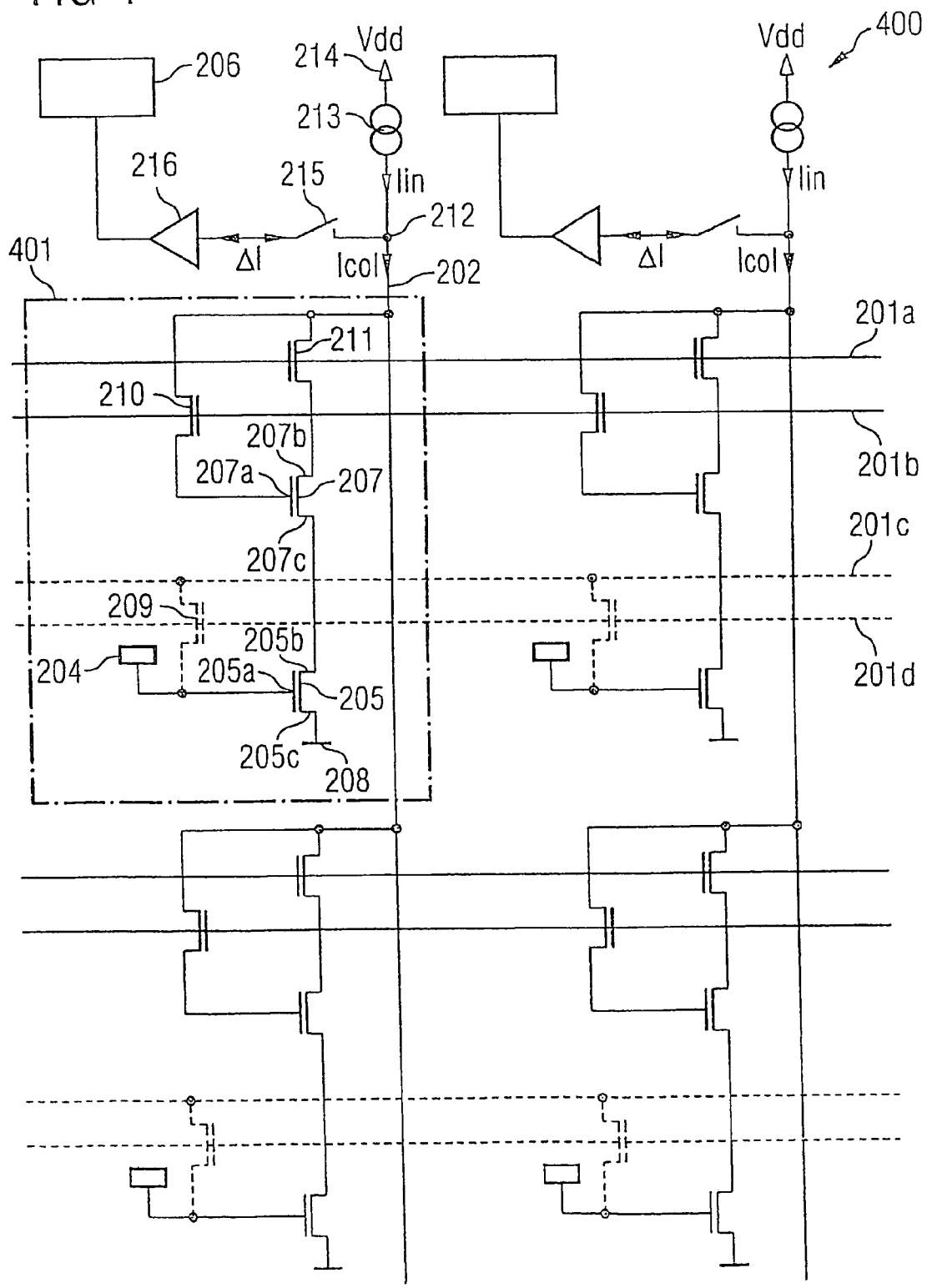

Clearly, in the case of the exemplary embodiment of the sensor array 400 as shown in FIG. 4, in the biosensor circuit arrangement 401, the calibration of the current through the first source/drain terminal 205b of the measuring transistor 205 is not achieved by means of a source negative feedback by the calibration transistor 207, as in FIG. 2, rather the calibration transistor 207 is utilized, in FIG. 4, as an element for setting the electrical potential of the first source/drain terminal 205b of the measuring transistor 205. In order that this control mechanism can be utilized efficiently, it is advantageous to choose for the measuring transistor 205 an operating point at which the intensity of the current flow through the first source/drain terminal 205b of the measuring transistor 205 depends to a sufficiently great extent on the electrical potential at the first source/drain terminal 205b of the measuring transistor 205. This is readily fulfilled for operating points in the triode region or in the linear region of the transistor characteristic curve. In other words, the biosensor circuit arrangement 401 operates particularly efficiently as a calibration device if the voltage between the gate terminal 205a and the second source/drain terminal 205c of the measuring transistor 205 minus the threshold voltage is greater than the voltage between the two source/drain terminals 205b, 205c of the measuring transistor 205. Furthermore, this is readily fulfilled for transistors having a sufficiently short channel length even in saturation operation, which is a consequence of short-channel effects. As far as the calibration transistor 207 is concerned, it is thus expedient to choose an operating point in the saturation region for said calibration transistor. In accordance with the configuration of the biosensor circuit arrangement 401 as shown in FIG. 4, the calibration transistor 207 is operated as a source follower, that is to say that the potential of the second source/drain terminal 207c of the calibration transistor 207 is offset by a defined magnitude compared with the potential at the gate terminal 207a (that is to say clearly follows the potential at the gate terminal) and is largely independent of the electrical potential at the first source/drain terminal 207b of the calibration transistor 207.

It should be noted that, for all the exemplary embodiments of the sensor array according to the invention and of the biosensor circuit arrangement according to the invention that are described here, the operating points of the transistors are effected by adjusting parameters in particular the geometrical parameters (e.g. width W and length L) of the measuring transistors and of the calibration transistors and also the current $I_{in}$ impressed into the respective column line 202.

A description is given below, with reference to FIG. 5, of the sensor array 500 shown therein in accordance with a fourth preferred exemplary embodiment of the invention.

Figure 5:
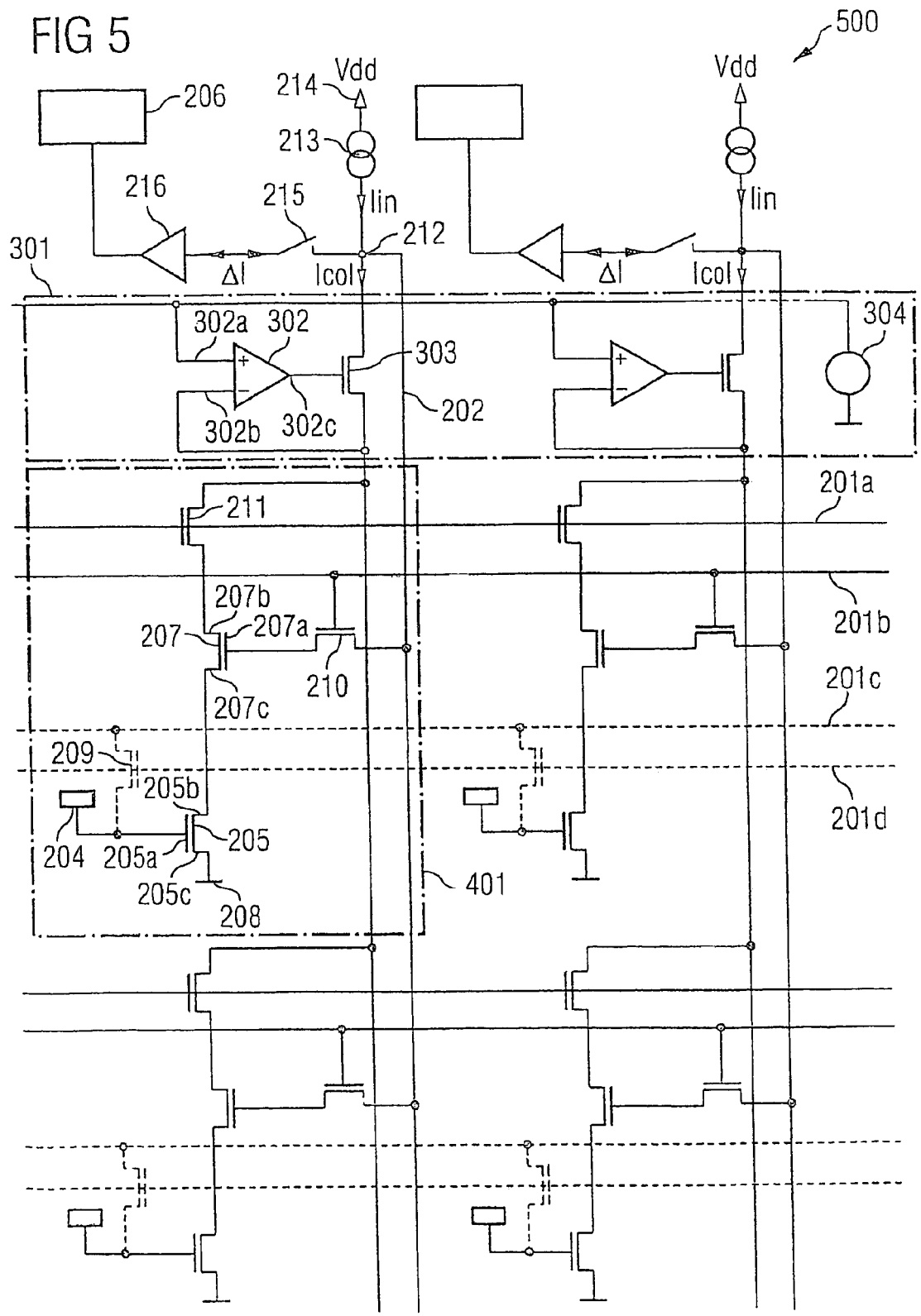

The sensor array 500 shown in FIG. 5 differs from the sensor array 400 shown in FIG. 4 merely in that the sensor array 500 additionally has a potential control device 301, which is described in detail above with reference to FIG. 3. Said potential control device has the functionality that the electrical potential of the column lines 202 can be regulated to a constant value. The functionality and the interconnection of the potential control device 301 and of the biosensor circuit arrangement 401 of the sensor array 500 are realized analogously to the interconnection of the potential control device 301 and the biosensor circuit arrangement 203 from FIG. 3.

A fifth preferred exemplary embodiment of the sensor array according to the invention is described below with reference to FIG. 6.

Figure 6:
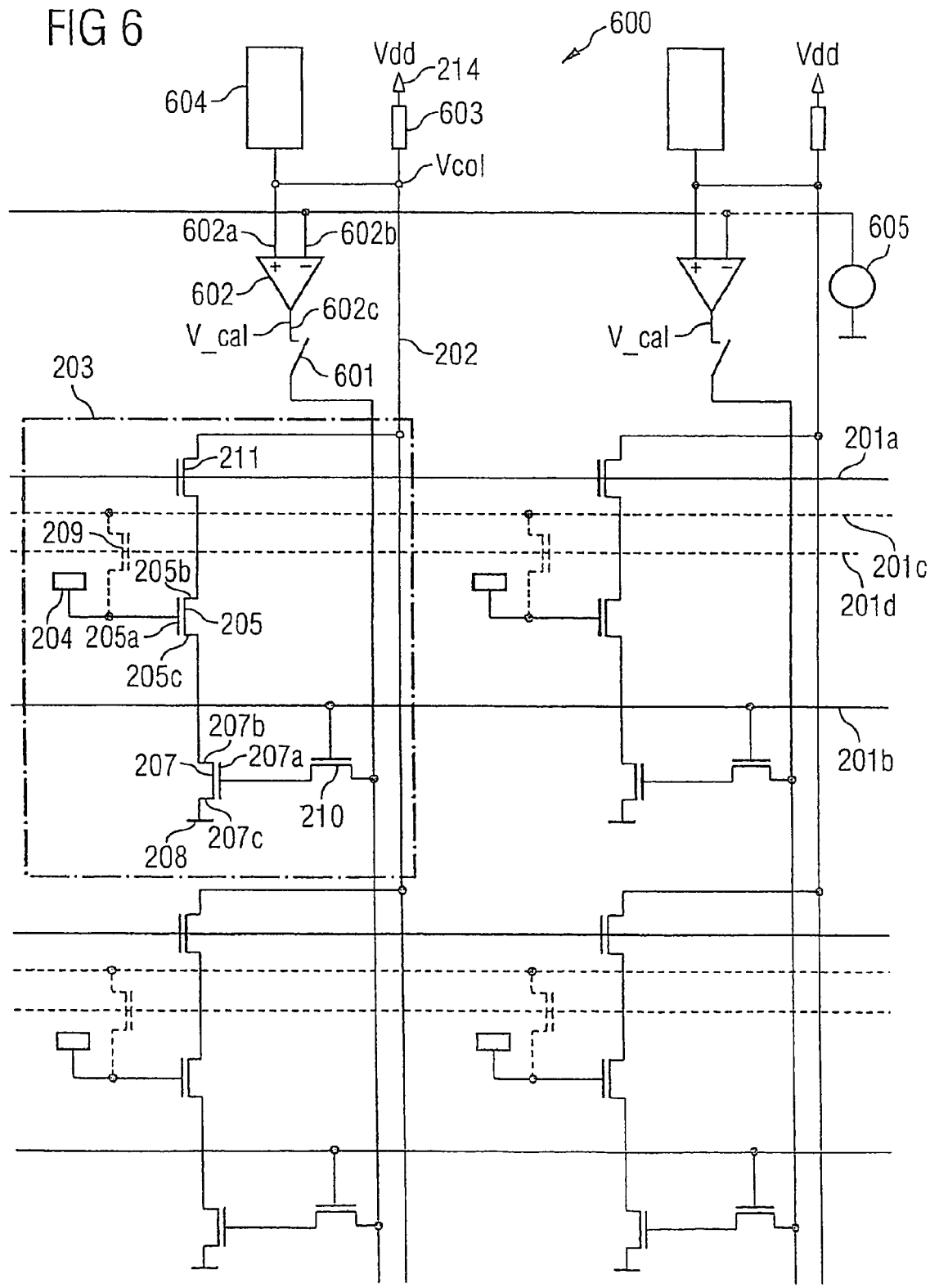

The sensor array 600 shown in FIG. 6 has biosensor circuit arrangements 203, each of which is designed like the biosensor circuit arrangements 203 shown in FIG. 2. However, the sensor signal detected in the case of the sensor array 600 is an electrical voltage, rather than an electric current as in the case of the sensor array 200. The modifications which are necessary in order to arrive at the sensor array 600 shown in FIG. 6 from the sensor array 200 shown in FIG. 2 are described below.

As already discussed, the interconnection within the biosensor circuit arrangement 203 is described analogously to that in FIG. 2. As shown in FIG. 6, that source/drain terminal of the second switching transistor 210 which is not coupled to the gate terminal 207a of the calibration transistor 207 is coupled to a second switch 601. The second switch 601 is coupled to the output 602c of an operational amplifier 602, the non-inverting input 602a of which is coupled both to a voltmeter 604 and to that source/drain terminal of the third selection transistor 211 which is not coupled to the first source/drain terminal 205b of the measuring transistor 205. The inverting input 602b of the operational amplifier 602 is coupled to a second voltage source 605, by means of which the inverting input 602b of the operational amplifier 602 is brought to a defined electrical potential. Furthermore, the non-inverting input 602a of the operational amplifier 602 is coupled to one terminal of a load element 603, preferably an electrical resistor, to the other terminal of which the supply voltage 214 is applied. In other words, in the case of the configuration shown in FIG. 6, compared with the configuration of the sensor array as shown in FIG. 2, the constant-current source 213 is replaced by the load element 603. Furthermore, the ammeter 206 is replaced by a voltmeter 604. The sensor current is converted into a voltage to be detected by means of the voltage drop across the load element 603. In other words, the sensor signal is an electrical voltage in the case of the sensor array 600.

The electric current which flows through a biosensor circuit arrangement 203 selected by means of the first row line 201a and the third switching transistor 211 brings about a voltage drop across the load element 603 both during a calibration phase and during a measurement phase in the circuit shown in FIG. 6. The output signal of a column line 202 is the electrical column voltage $V_{col}$. In the case of the sensor array 600 as well, the biosensor circuit arrangements 203 of a row are selected by the associated third switching transistors 211 being brought to an on state by means of an electrical signal on one of the first row lines 201a. In the case of the sensor array 600, preferably precisely one row of biosensor circuit arrangements 203 is connected in, that is to say that there is present on the associated first row line 201a an electrical signal that puts the third switching transistors 211 coupled thereto into an on state, whereas such an electrical signal is not present in this case on the other first row lines 201a (the other rows of biosensor circuit arrangements 203).

In a calibration phase for calibrating the biosensor circuit arrangement 203 of a row of biosensor circuit arrangements, in the case of the row to be selected, the corresponding row line 201b has applied to it an electrical signal such that the associated second switching transistors 210 are thereby turned on, whereas such an electrical signal is not applied to the second row lines 201b of a row of biosensor circuit arrangements 203 that is not to be selected. The second switch 601 is closed in the calibration phase. The interconnection of the biosensor circuit arrangements 203 with the operational amplifier 602 and the load element 603 in the manner described above once again brings about a closed control circuit. A voltage is provided at the output 602c of the operational amplifier 602, which voltage is applied to the gate terminal 207a of the calibration transistor 207 via the turned-on second switching transistor 210. This voltage defines the conductivity state of the calibration transistor 207, which, as in the case of the sensor array 200, is operated as a controllable resistor. This brings about a source negative feedback of the measuring transistor 205, so that the electric current through the measuring transistor 205 and through the calibration transistor 207 is set in such a way that a voltage drop produced across the load element 603 is such that the differential voltage at the inputs 602a, 602b of the operational amplifier 602 results in zero, whereby $V_{col}$ is equal to the electrical potential applied to the inverted input 602b by means of the second voltage source 605. This has the effect that the output voltage of a sensor element or a biosensor circuit arrangement 203, that is to say the electrical voltage on the signal-carrying column line 202, is set to a predetermined value independently or the threshold voltage of the measuring transistor 205 (or another or a further or a plurality of further physical parameters of the measuring transistor 205 or other components) of a specific biosensor circuit arrangement 203 and independently of the precise resistance of the load element 603. If this state has formed stably in the sensor array 600, the electrical signal on the second column line 201b is removed, so that the second switching transistor 210 is turned off. However, the charge applied during the calibration phase described above remains on the gate capacitance, that is to say on the gate terminal 207a of the calibration transistor 207, that is to say that the electrical potential of the gate terminal 207a remains unchanged, so that the associated biosensor circuit arrangement 203 is calibrated.

After the conclusion of the calibration phase, the second switch 601 can be opened. Although the opening or deactivation of the regulating circuit is also brought about by the fact that the electrical signal on the second row line 201b is switched off, the operation of a non-closed regulating circuit may lead to undesirably large voltage swings at the output 602c of the operational amplifier 602, as a result of which interference signals may couple over onto the signal-carrying lines 202 from lines utilized during the calibration phase for providing the electrical gate potential of the calibration transistor 207. This undesirable effect is referred to as crosstalk and can be avoided by opening the second switch 601 after the end of the calibration phase.

In the case of the sensor array 600, the operating point of the measuring transistor 205 is preferably to be chosen in the saturation region. However, the regulating and calibrating mechanism described also functions when the operation point of the measuring transistor 205 is chosen outside the saturation region.

In the measurement phase, changes in the potential V(E) at the sensor electrode 204 on account of a sensor event, for example on account of a current of electrically charged particles through the ion channels of the membrane of a nerve cell onto the active sensor surface of the sensor array 600, once again lead to a change in the current flow through the first source/drain terminal 205b of the measuring transistor 205 and thus to a change in the current flow through the associated column line 202, thereby effecting a corresponding voltage drop across the load element 603.

A sixth preferred exemplary embodiment of the sensor array according to the invention is described below with reference to FIG. 7.

Figure 7:
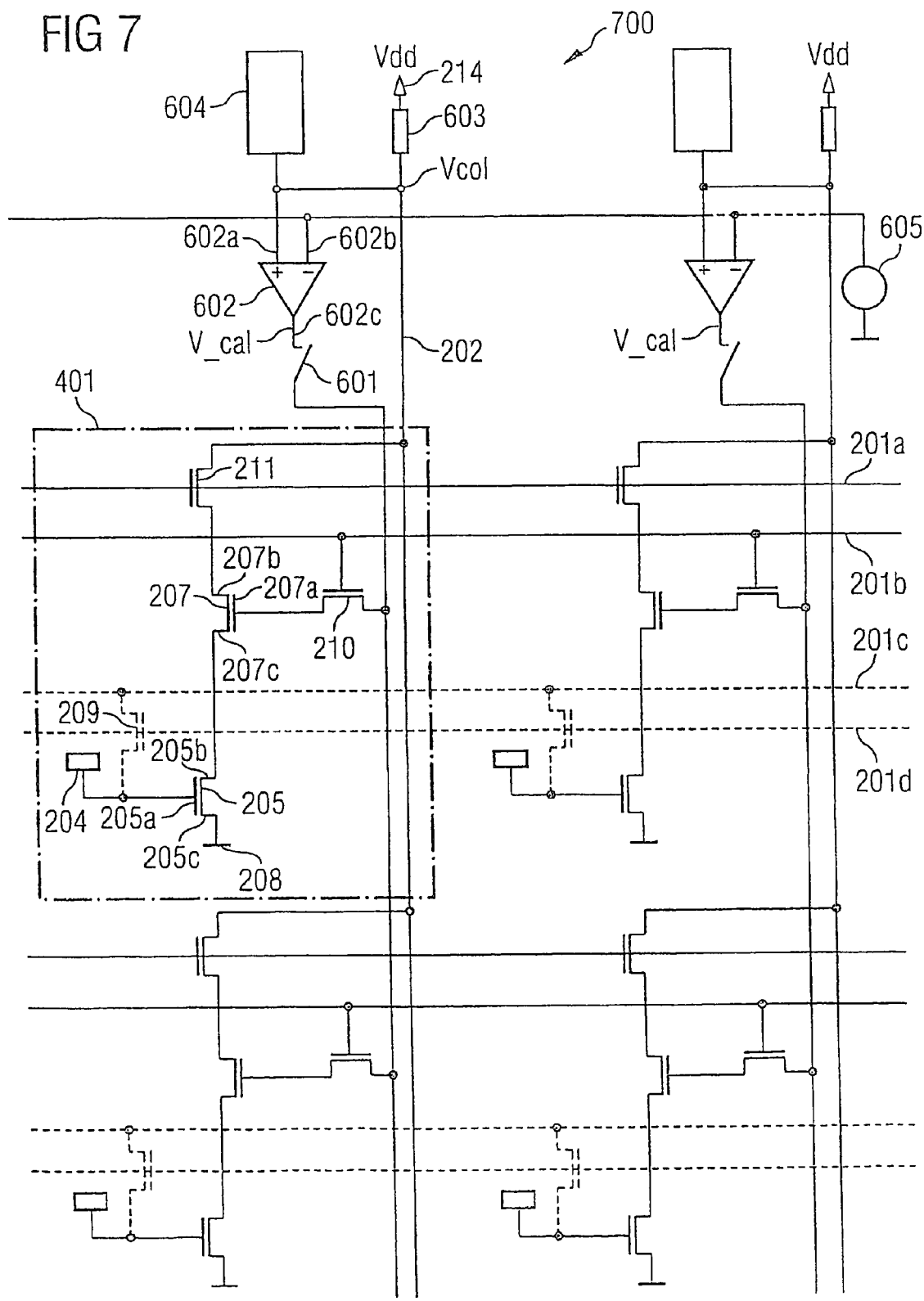

The sensor array 700 shown in FIG. 7 has a biosensor circuit arrangement 401 as has been described above with reference to FIG. 4 for the sensor array 400. Furthermore, the sensor signal in the case of the sensor array 700 is an electrical voltage, as in the case of the sensor array 600. In this case, the load element 603 is coupled to that source/drain terminal of the third switching transistor 211 which is not coupled to the first source/drain terminal 207b of the calibration transistor 207, and the second switch 601 is coupled to that source/drain terminal of the second switching transistor 210 which is not coupled to the gate terminal 207a of the calibration transistor 207.

The functionality of the sensor array 700 results from a combination of the above descriptions of the sensor array 400 and the sensor array 600. Clearly, the positions of the measuring transistor 205 and of the switching transistor 207 in the case of the sensor array 700 are "interchanged" relative to one another compared with the sensor array 600, that is to say that, in the case of the sensor array 700, the calibration is not achieved by means of a source negative feedback of the measuring transistor 205 by the calibration transistor 207, rather the calibration transistor 207 is utilized here as an element for setting the electrical potential of the first source/drain terminal 205b of the measuring transistor 205. The operating points of the transistors involved, in particular of the measuring transistor 205 and of the calibration transistor 207, are therefore to be chosen in the manner described above for the sensor array 400.

A seventh exemplary embodiment of the sensor array according to the invention is described below with reference to FIG. 8.

Figure 8:
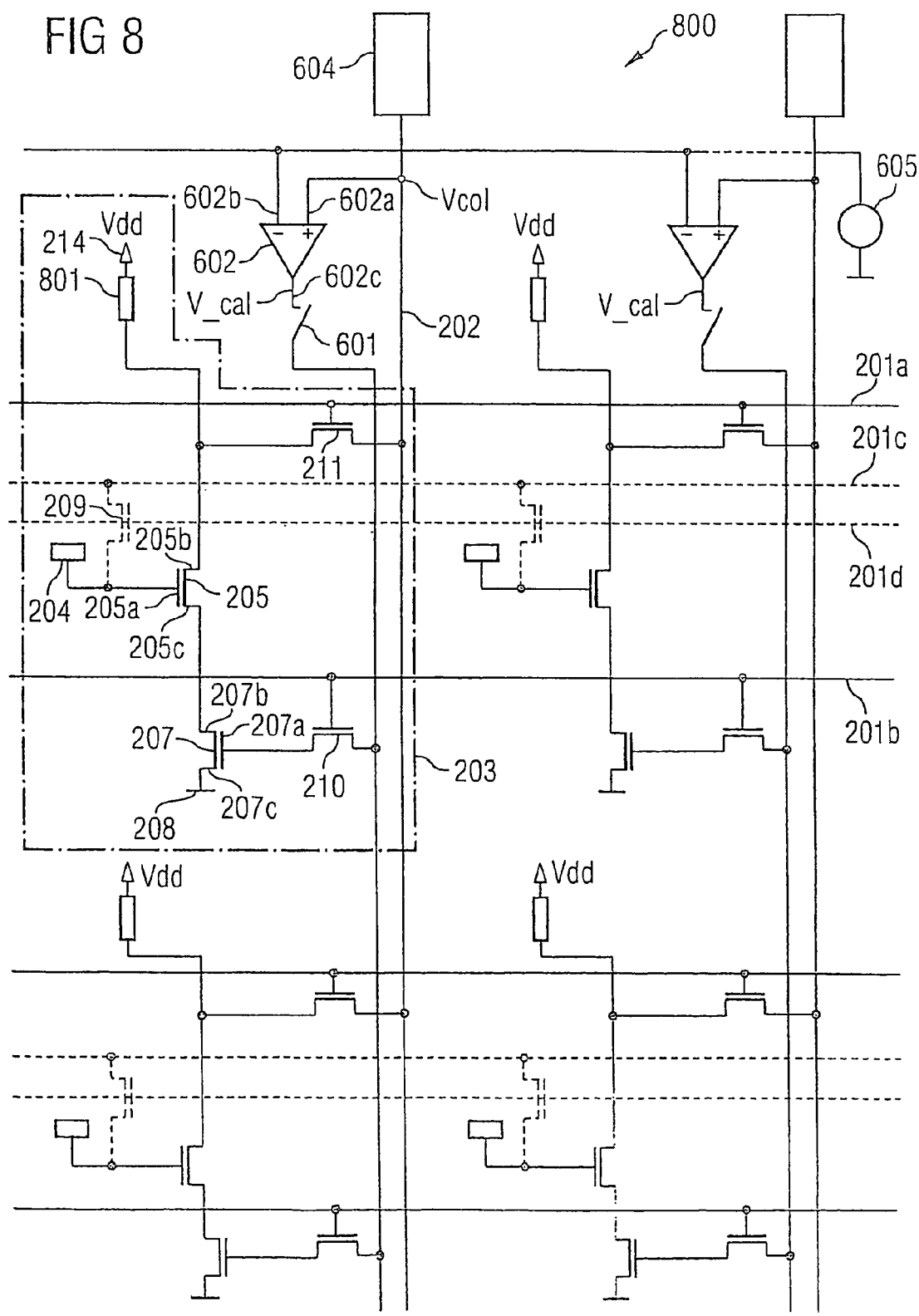

The sensor array 800 shown in FIG. 8 differs only in points from the sensor array 600 shown in FIG. 6. In particular, the biosensor circuit arrangements 203 are formed in largely identical fashion in both exemplary embodiments of the sensor arrays 600, 800, the biosensor circuit arrangement 203 shown in FIG. 8 additionally having a dedicated load element 801 in comparison with the biosensor circuit arrangement 203 shown in FIG. 6. Moreover, a voltage signal $V_{col}$ is detected as sensor signal in both cases. Moreover, the sensor array 800 has the operational amplifier 602 which is connected up to the biosensor circuit arrangement 203 as in the case of the sensor array 600. However, in the case of the sensor array 800, each biosensor circuit arrangement 203 is assigned a load element 801 contained therein, one terminal of which is coupled to the first source/drain terminal 205b of the associated measuring transistor 205, and to the other terminal of which the electrical potential of the supply voltage 214 is applied.

In other words, the sensor array 800 is altered with respect to the sensor array 600 to the effect that a common load element 603 per column line 202 is not utilized by all the biosensor circuit arrangements 203 of a column line 202, rather each biosensor circuit arrangement 203 has an individual load element 801 in the case of the sensor array 800. It must be emphasized that parameter fluctuations in the case of the individual load elements 801 are likewise compensated for by the calibration. In other words, the nonreactive resistance of the load element 801 may be regarded as a physical parameter whose value is different in different biosensor circuit arrangements 203, this difference or this alteration of the value of the physical parameter being at least partly compensated for by the calibration. With regard to the calibration phase, the measurement phase and the setting or choice of the operating points of the transistors, in particular of the measuring transistor 205 and of the calibration transistor 207, reference shall be made to the above description of the sensor array 200.

It should be pointed out that the transistors in the sensor arrays 200 to 800 are all formed as n-MOS field-effect transistors. The fact that, instead of an n-MOS transistor, with slight constructional changes, each of the transistors, in particular the measuring transistor and the calibration transistor, may be formed as a p-MOS transistor is shown by way of example in the sensor array 900 shown in FIG. 9, which is described below.

Figure 9:
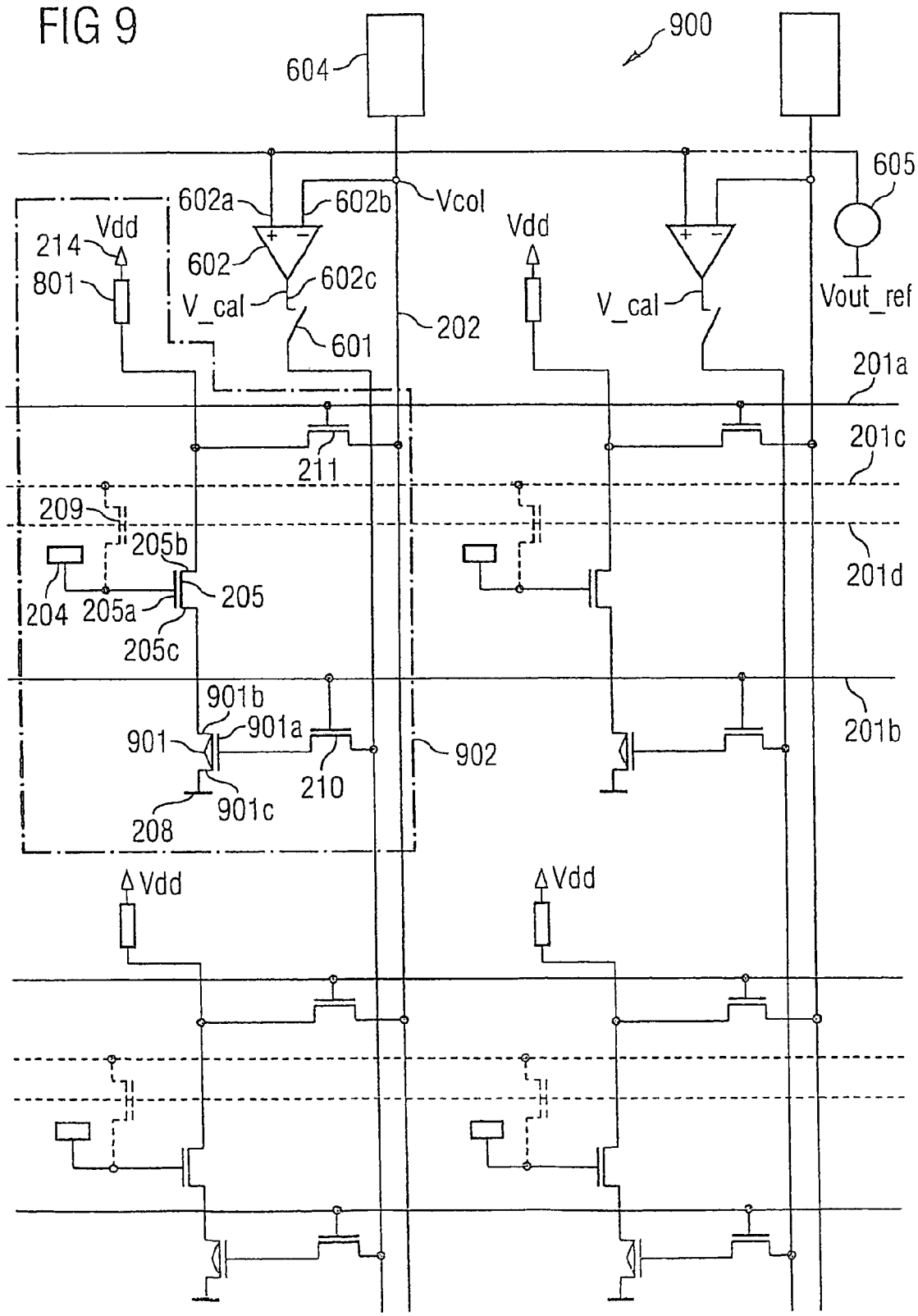

The sensor array 900 is formed in a similar manner to the sensor array 800. In contrast to the sensor array 800, however, the sensor array 900 has a p-MOS calibration transistor 901 formed as a p-MOS transistor. A description is given below, with reference to FIG. 9, of how the interconnection of the components of the sensor array 900 has to be altered in order to use a p-MOS transistor 901 as a calibration transistor. In the case of the biosensor circuit arrangement 902, the p-MOS calibration transistor 901, which has a gate terminal 901a, a first source/drain terminal 901b and a second source/drain terminal 901c, is connected up, with regard to the adjacent components directly adjoining it, like the n-MOS calibration transistor 208 shown in FIG. 8. However, the interconnection of the operational amplifier 602 is modified in order to take account of the fact that the calibration transistor formed as an n-MOS transistor in accordance with FIG. 8 is formed as a p-MOS calibration transistor 901 in the case of the sensor array 900. As shown in FIG. 9, the inverted input 602b of the operational amplifier 602 (differently than in FIG. 8) is coupled to that source/drain terminal of the third switching transistor 211 which is not coupled to the first source/drain terminal 205b of the measuring transistor 205. By contrast, the non-inverted input 602a of the operational amplifier 602 is coupled to the second voltage source 605. Apart from this aspect, the biosensor circuit arrangement 902 with the p-MOS calibration transistor 901 is constructed and interconnected identically to the biosensor circuit arrangement 209 from FIG. 8. In other words, on account of the replacement of the n-MOS calibration transistor 207 from FIG. 8 by the p-MOS calibration transistor 901 from FIG. 9, the inverted input 602b is to be interchanged with the non-inverted input 602a of the operational amplifier 602 of each column line 202. The possibility of optionally being able to use p-MOS or n-MOS transistors as transistor for the sensor array according to the invention enables the sensor array to be set flexibly to the requirements of the individual case. In particular, parameters such as the available space requirement and other boundary conditions can thereby be flexibly taken into account.

A ninth preferred exemplary embodiment of the sensor array according to the invention is described below with reference to FIG. 10.

The sensor array 1000 has a plurality of biosensor circuit arrangements 1003 which are arranged essentially in matrix form in crossover regions of row lines 1001a, 1001b and column lines 1002a, 1002b and are connected up to the row and column lines 1001a, 1001b, 1002a, 1002b. A biosensor circuit arrangement 1003 is formed on or in a substrate (not shown in FIG. 10) and has a sensor element having a physical parameter which can be coupled to a substance to be examined, the type of coupling having a resistive component. Furthermore, each biosensor circuit arrangement 1003 has a calibration device which is formed in or on the substrate and is set up in such a way that it can be used to at least partly compensate for an alteration of the value of the physical parameter of the sensor element. The sensor element is constructed from an electrically conductive sensor electrode 1004 that can be coupled to the substance to be examined and from a measuring transistor 1005, the gate terminal 1501 of which is coupled to the electrically conductive sensor electrode 1004 made of platinum. Furthermore, a first source/drain terminal 1005b of the measuring transistor 1005 can be coupled (via other components) to a first ammeter 1006. The calibration device of each biosensor circuit arrangement 1003 is set up in such a way that it can be used to control the electrical potential present at a second source/drain terminal 1005c of the measuring transistor 1005. Furthermore, the calibration device of each biosensor circuit arrangement 1003 has a calibration transistor 1007, a first constant-current source 1008, which is coupled to respective second source/drain terminals 1005c, 1007c of the measuring and calibration transistors 1005, 1007 that are connected in parallel with one another, for providing a predetermined electrical current intensity $I_{Bias}$, and a current mirror circuit coupled to respective first source/drain terminals 1005b, 1007b of the measuring and calibration transistors 1005, 1007 that are connected in parallel with one another, which is connected up in such a way that it can be used to set, for the purpose of at least partly compensating for the alteration of the value of the physical parameter (the threshold voltage of the measuring transistor 1005), the electrical potential at the gate terminal 1007a of the calibration transistor 1007 in such a way that, in the absence of a sensor event, the current flows between the two source/drain terminals of the measuring transistor 1005b, 1005c and calibration transistor 1007b, 1007c thereof are identical. It should be pointed out that, in accordance with the exemplary embodiment described, a common current mirror circuit and further common elements are provided jointly for each column of biosensor circuit arrangements 1003, as described below.

The functionality of the sensor array 1000 is described below. As in the previously described exemplary embodiments, too, a biosensor circuit arrangement 1003 can be selected by the first row line 1001a having applied to it an electrical signal such that a first and a second selection transistor 1009a, 1009b are thereby turned on. The first and second switching transistors 1009a, 1009b function as switches and close if a corresponding electrical signal is applied to the first row line 1001a. The first constant-current source 1008 is formed from a first auxiliary transistor 1010 and a bias voltage source 1011. In this case the first auxiliary transistor 1010 is operated in saturation. The electrical potential of the bias voltage source 1011 is applied to the gate terminal of the first auxiliary transistor 1010, a first source/drain terminal of the first auxiliary transistor 1008 is grounded, and a second source/drain terminal of the first auxiliary transistor 1008 is coupled to the second source/drain terminals 1005c, 1007c of the measuring transistor 1005 and of the calibration transistor 1007. The constant current provided to an electrical node 1012 by the constant-current source 1008 is designated at $I_{Bias}$. The measuring transistor 1005 is preferably operated in saturation. If the voltage at the sensor electrode 1004 and thus at the gate terminal 1005a of the measuring transistor 1005 changes, then the current flow between the two source/drain terminals 1005b, 1005c is thereby influenced characteristically. Since the total current $I_{Bias}$ through the source/drain terminals 1005b, 1005c of the measuring transistor 1005 and through the source/drain terminals 1007b, 1007c of the calibration transistor 1007 is constant, a sensor signal occurs both in the current path of the measuring transistor and in the current path of the calibration transistor 1007. However, the sensor signal leads to an increase in one of the two parallel current paths and to a corresponding decrease of the current intensity in the other current path by a differential value that is characteristic of the sensor event. The two current flows through the measuring transistor 1005 and through the calibration transistor 1007 are conducted through the turned-on first and second switching transistors 1009a, 1009b, a respective source/drain terminal of which is coupled to the first source/drain terminal of the measuring transistor and of the calibration transistor 1005b and 1007b respectively, and can be detected by the first ammeter 1006 coupled to the other source/drain terminal of the first switching transistor 1009a and, respectively, by a second ammeter 1013 coupled to the other source/drain terminal of the second switching transistor 1009b, if neither a first switch 1014 nor a second switch 1015 are in the position shown in FIG. 10 (but rather in the position complementary thereto). It is then possible to detect the current flow through the measuring transistor 1005 by means of the first ammeter 1006 and the current flow through the calibration transistor 1007 by means of the second ammeter 1013. Owing to an improved robustness in respect of errors, the formation of the difference between these two detected current intensities, that is to say a differential signal processing, affords an increased measurement accuracy which is particularly important for the small measurement signals to be expected in the case of biological samples.

Figure 10:
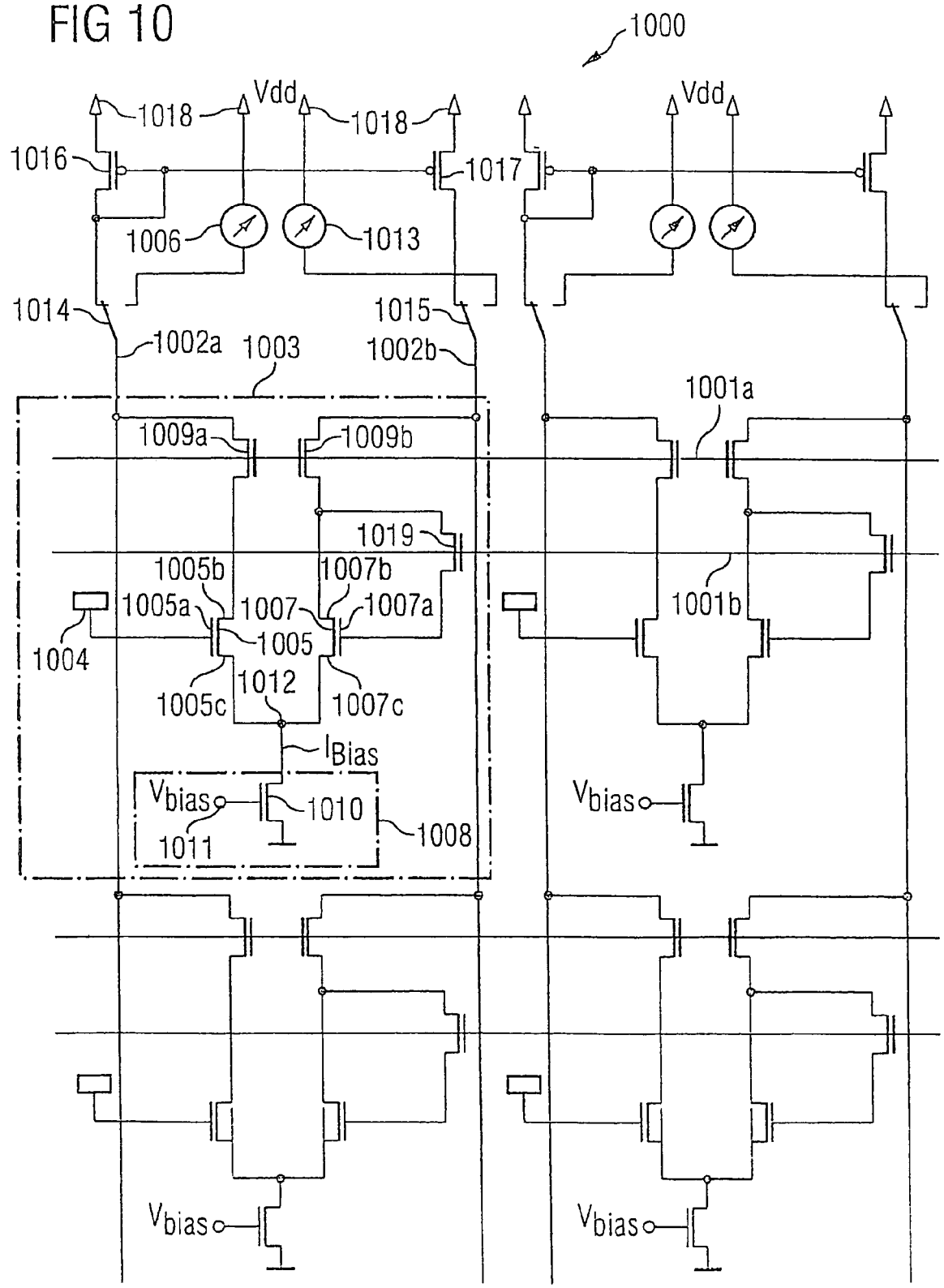

In the case of the sensor array 1000, the biosensor circuit arrangements 1003 are calibrated using a current mirror circuit, which is connected up in the manner shown in FIG. 10 and has a first and a second current mirror transistor 1016, 1017. If the first switch 1014 is in the switch position shown in FIG. 10, then that source/drain terminal of the first switching transistor 1009a which is not coupled to the first source/drain terminal 1005b of the measuring transistor 1005 is coupled both to a source/drain terminal and to the gate terminal of the first current mirror transistor 1016. Furthermore, the gate terminal of the first current mirror transistor 1016 is coupled to the gate terminal of the second current mirror transistor 1017. In the switch position of the second switch 1015 as shown in FIG. 10, that source/drain terminal of the second auxiliary transistor 1009b which is not coupled to the first source/drain terminal of the calibration transistor 1007 is coupled to a source/drain terminal 1007b of the second current mirror transistor 1017. Furthermore, in the case of the sensor array 1000, the electrical potential of a supply voltage 1018 is applied to the respective other source/drain terminals of the first current mirror transistor 1016 and of the second current mirror transistor 1017 and also to a respective terminal of the two ammeters 1006, 1013.

A description is given below of how a calibration is carried out using the two current mirror transistors 1016, 1017 and the interconnection thereof with the biosensor circuit arrangements 1003 in the manner shown in FIG. 10. In the calibration mode, the switch position of the first switch 1014 and of the second switch 1015 is as shown in FIG. 10. In order to select a specific biosensor circuit arrangement 1003 for calibration, a corresponding electrical signal is applied to a corresponding first row line 1001a, so that the first and second switching transistors 1009a, 1009b are turned on. On account of fluctuations of the electrical transistor parameters of the measuring transistor 1005 and of the calibration transistor 1007 (for example the threshold voltage), the current flow through the two branches of the differential pair, that is to say between the two source/drain terminals 1005b, 1005c of the measuring transistor 1005, on the one hand, and between the two source/drain terminals 1007b, 1007c of the calibration transistor 1007, on the other hand, will generally not be identical even when an identical electrical potential is applied to the gate terminals 1005a and 1007a of the measuring transistor 1005 and of the calibration transistor 1007, respectively. By means of the current mirror circuit, the output current through the source/drain terminals of the measuring transistor 1005 is inverted and compared with the current through the source/drain terminals of the calibration transistor 1007 from the other part. If a difference which differs from zero occurs between these two current intensities, then, in the case of a third switching transistor 1019 that is turned on on account of an electrical signal on one of the second column lines 1001b, the potential at the gate terminal 1007a of the calibration transistor 1007 changes until the same current flows in both paths of the differential pair. The gate terminal of the third switching transistor 1019 is coupled to the second row line 1001b, and its two source/drain terminals are connected between the gate terminal 1007a of the calibration transistor 1007 and the second switching transistor 1009b. If the electrical signal on the second column line 1000b is removed, then the third switching transistor 1019 is turned off and the calibration voltage or the calibration charge remains at the gate terminal 1007a of the calibration transistor 1007 so that the same current $I_{Bias}/2$ flows on both paths, that is to say through the measuring transistor 1005, on the one hand, and the calibration transistor 1007 on the other hand. The biosensor circuit arrangement 1003 is thereby calibrated.

Figure 11:
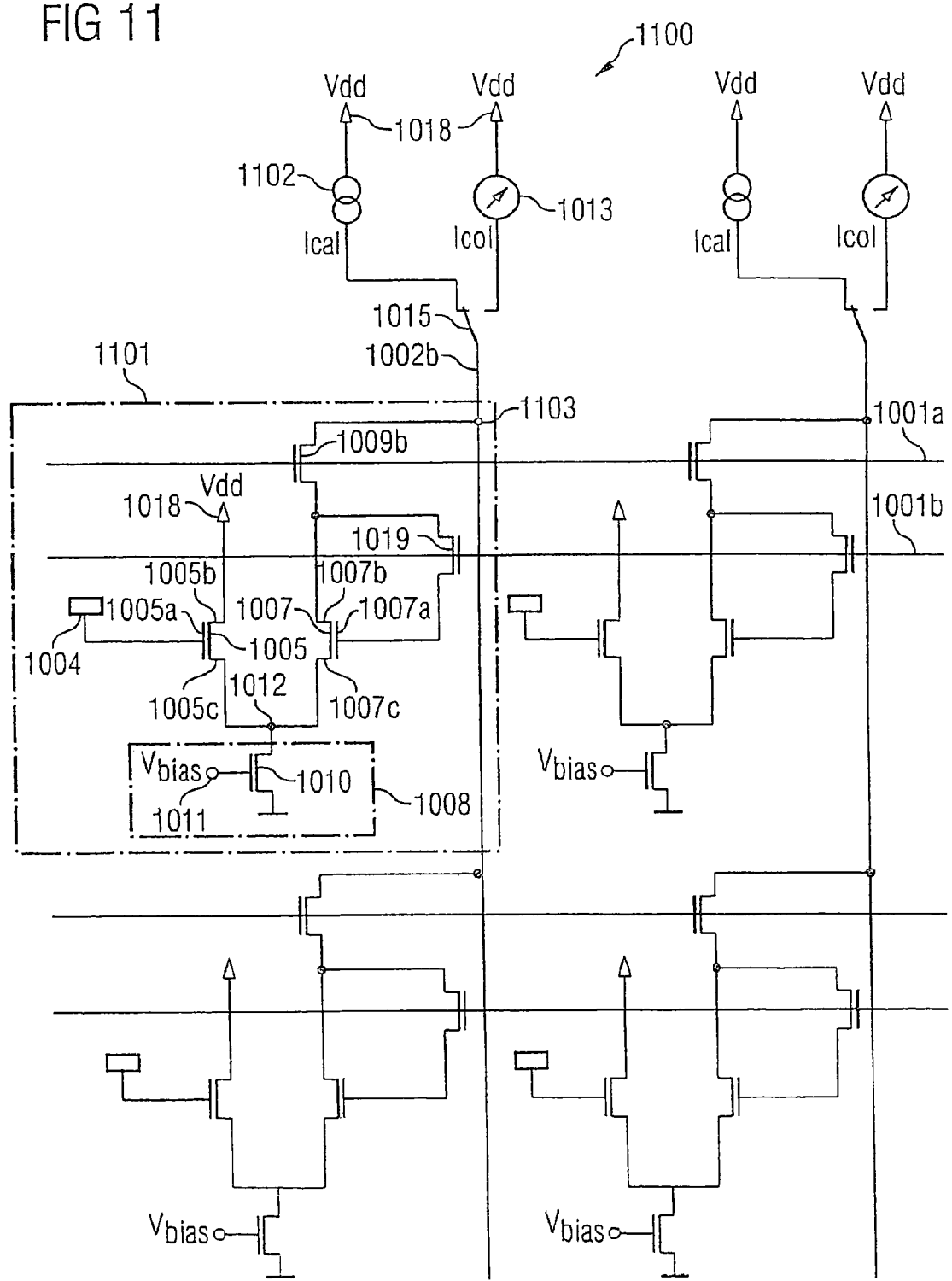

FIG. 11 shows a tenth exemplary embodiment of the sensor array according to the invention.

The sensor array 1100 again has a plurality of biosensor circuit arrangements 1101 arranged essentially in matrix form, which are modified compared with the biosensor circuit arrangements 1003 in FIG. 10. In particular, the electrical potential of a supply voltage 1018 is applied to the first source/drain terminal 1005b of the measuring transistor 1005. The components of the current mirror circuit in the current path of the measuring transistor 1005 are dispensable in the case of the sensor array 1100. The interconnection of the current path in which the calibration transistor 1007 is arranged corresponds, within the biosensor circuit arrangement 1001, to the configuration from FIG. 10. In other words, a sensor signal of the biosensor circuit arrangement 1101 can be applied to the second switch 1015, which is either in the position shown in FIG. 11 if the sensor array 110 is operated in the calibration phase, or in the opposite position thereto if the sensor array 1100 is operated in the measurement phase.

In the calibration phase, that source/drain terminal of the second switching transistor 1009b which is not coupled to the first source/drain terminal 1107b of the calibration transistor 1007 is coupled to one terminal of the second constant-current source 1102, the other terminal of which is brought to the electrical potential of the supply voltage 1018. In the measurement phase, in contrast, the described source/drain terminal of the second switching transistor 1009b is coupled to a terminal of the second ammeter 1013.

In the case of the biosensor circuit arrangement 1101, the potential of the supply voltage 1018 is thus applied to the first source/drain terminal 1005b of the measuring transistors 1005, and the calibration device has: the calibration transistor 1007 having the first source/drain terminal 1007b and the second source/drain terminal 1007c, the first constant-current source 1008, which is coupled to the second source/drain terminals 1005c and 1007c of the measuring and calibration transistors 1005, 1007 that are connected in parallel with one another, for providing a predeterminable electrical current intensity, and a second constant-current source 1102, which can be coupled to the first source/drain terminal 1007b of the calibration transistor 1007, for providing a further predeterminable electrical current intensity, which second constant-current source 1102 is connected up in such a way that it can be used to set, for the purpose of at least partly compensating for the alteration of the value of the physical parameter, the potentials that can be applied to the terminals of the transistors 1005, 1007 in such a way that, in the absence of a sensor event at the sensor electrode 1004, the current flows between the two source/drain terminals 1005b, 1005c of the measuring transistor 1005 and between the two source/drain terminals 1007b, 1007c of the calibration transistor 1007 are identical.

Clearly in the case of the sensor array 1100, in contrast to the sensor array 1000, only one of the two current paths of the measuring transistor 1005 and of the calibration transistor 1007, namely—in accordance with FIG. 11—only the current path between the source/drain terminals 1007b, 1007c of the calibration transistor 1007, is led out of the biosensor circuit arrangement 1101. A row of biosensor circuit arrangements 1101 is again selected by the first row line 1001a having applied to it an electrical signal such that the second switching transistor 1009b is thereby turned on. At the upper edge section of the sensor array 1100 in accordance with FIG. 11, the current flow through the current path of the calibration transistor 1007 is then measured and evaluated by means of the second ammeter 1013 in the corresponding switch position (opposite switch position of the second switch 1015 to that in FIG. 11).

In the case of the sensor array 1100, the calibration is effected by impressing a reference current $I_{cal}$. Preferably, this calibration current is half as large as the current of the first constant-current source 1008 of the biosensor circuit arrangement 1101, that is to say $I_{cal}=I_{Bias}/2$. It is then ensured that a current $I_{Bias}/2$ also flows in the measurement branch of the differential pair with the measuring transistor 1005. In order also to compensate for statistical fluctuations of the constant current $I_{Bias}$ (for example on account of a variation of the threshold voltage of the first auxiliary transistor 1010), this may firstly be measured at an edge section of the sensor array 1100. For this purpose, in the calibration phase, the electrical voltage at an electrical output node 1103 of a biosensor circuit arrangement 1101 and thus at the gate terminal 1007a of the calibration transistor 1007 is chosen to have a magnitude such that the entire or approximately the entire current $I_{Bias}$ of the first constant-current source 1008 flows through this path. Afterward, a current $I_{col}<I_{Bias}$ is impressed on this path, thus resulting in a current through the measuring transistor 1005 having the value $I_{Bias}-I_{cal}$. After the end of the calibration phase, that is to say after the removal of the electrical signal on the second row line 1001b, on account of which signal the third switching transistor 1019 had previously been turned on, the third switching transistor 1019 is turned off and, therefore, the previously impressed charge state remains stored at the gate terminal 1007a of the calibration transistor 1007 and the biosensor circuit arrangement 1101 is calibrated.

The sensor array 1100 shown in FIG. 11 has the advantage over the sensor array shown in FIG. 10 that some components are saved, so that the sensor array 1100 is less complicated to produce. By contrast, the sensor array 1100 shown in FIG. 10 has a particularly high detection sensitivity on account of the differentiated current measurement.

Figure 12:
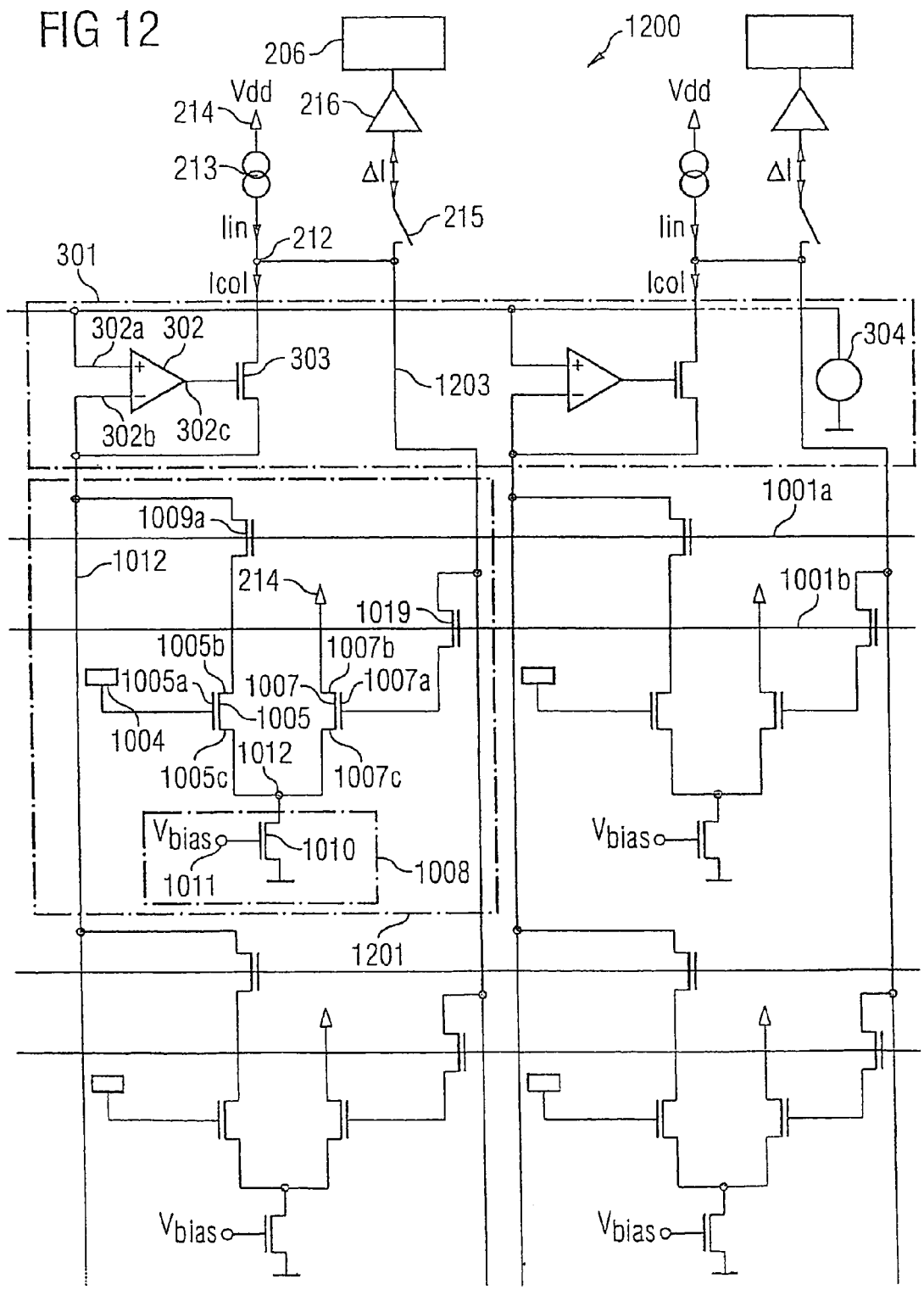

FIG. 12 shows a sensor array 1200 in accordance with an eleventh preferred exemplary embodiment of the invention.

The sensor array 1200 has a multiplicity of biosensor circuit arrangements 1201 arranged in matrix form, which are in part constructed and interconnected like the biosensor circuit arrangements 1101 shown in FIG. 11. However, the sensor array 1200 is provided with a potential control device 301 for keeping the potential of the column lines 1202 constant: in the case of the sensor array 1200, a calibration voltage is fed via an additional column line 1203 in a manner similar to that in FIGS. 6 to 9, and the potential of the column line 1202 is held at a constant electrical potential, provided by the first voltage source 304, by means of a potential control device 301 in a manner analogous to the concept of FIG. 3. The electrical potential of the supply voltage 214 is applied to the first source/drain terminal 1007b of the calibration transistor 1007.

Figure 13:
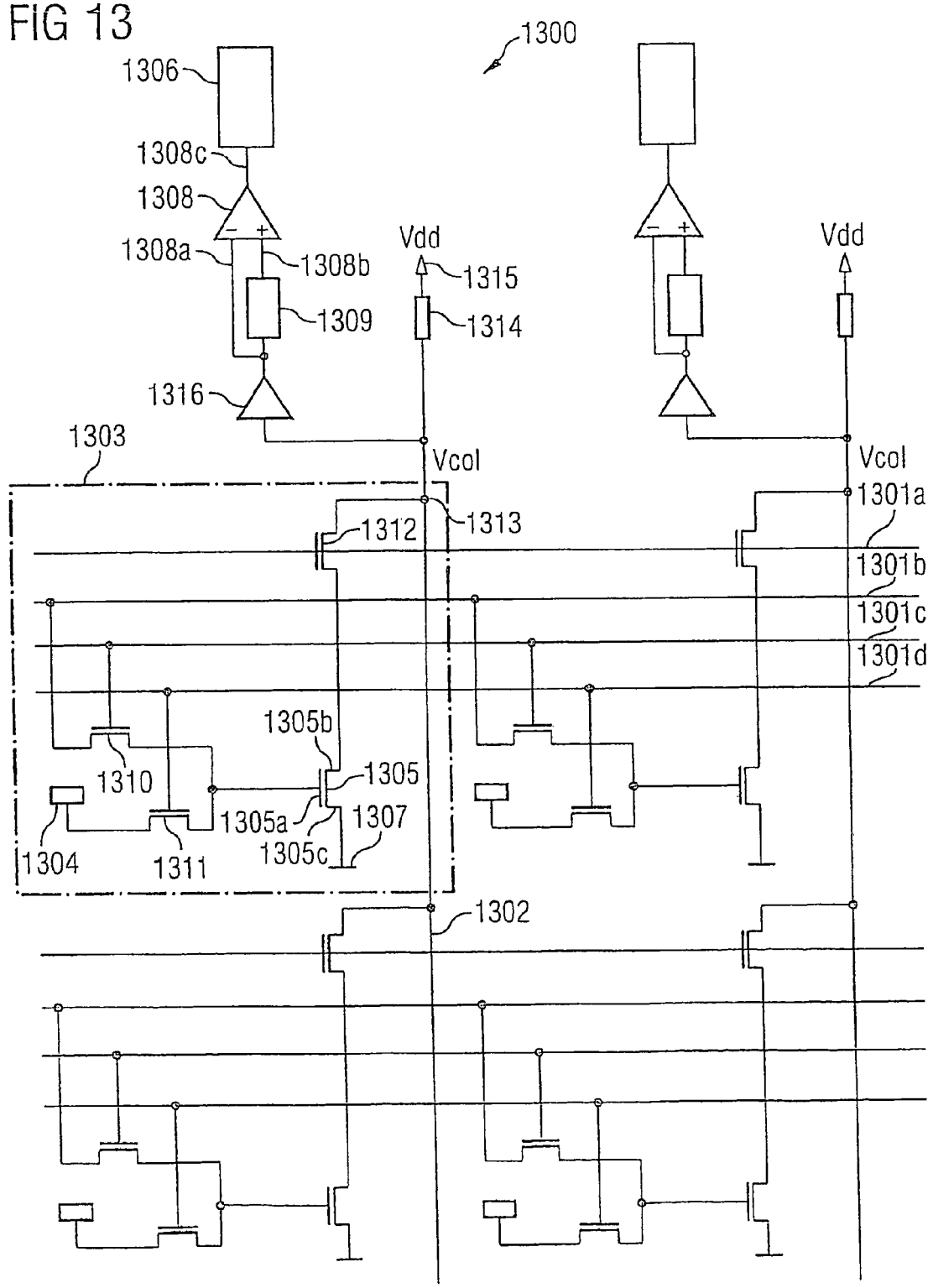
Figure 14:
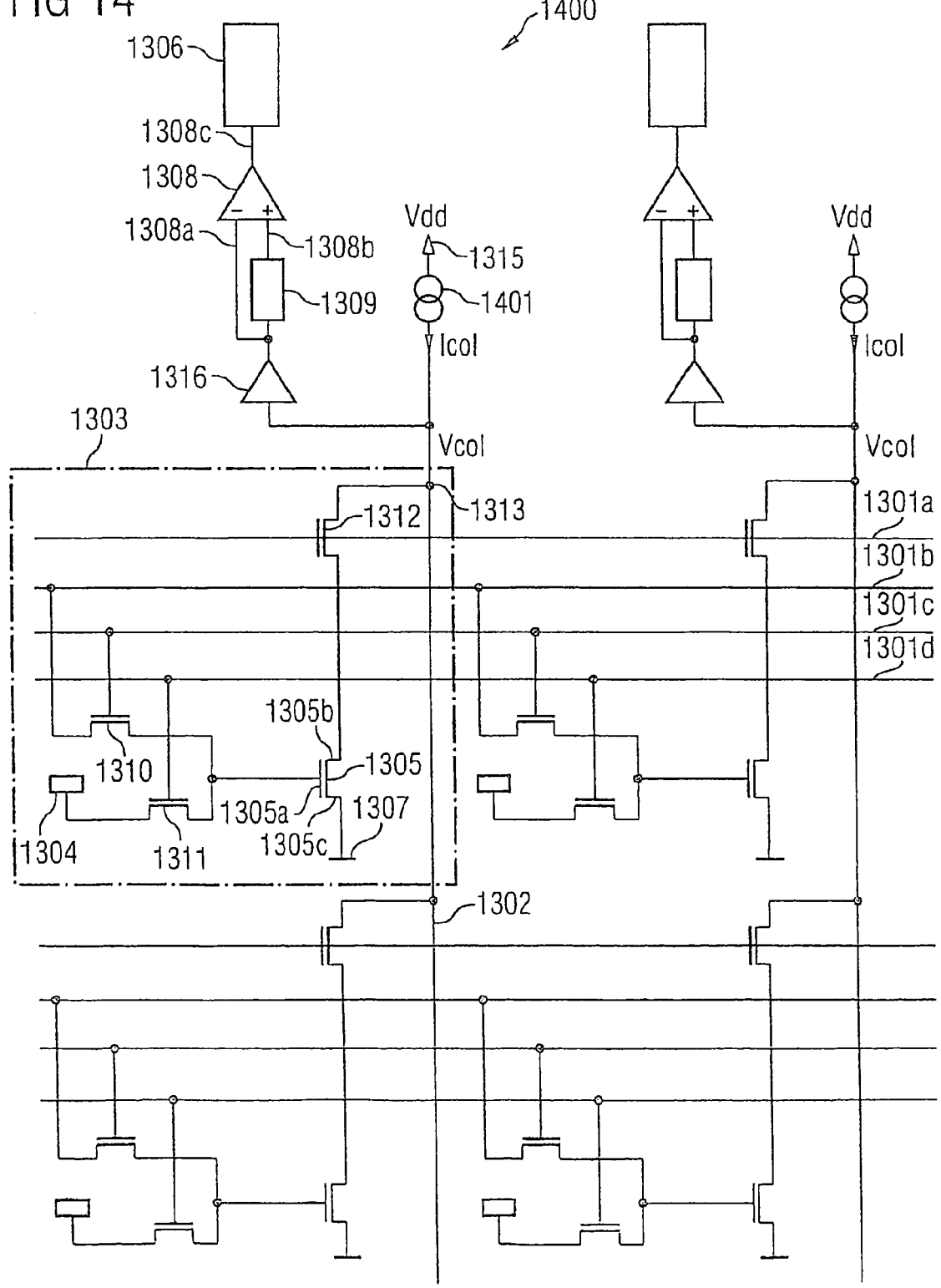
Figure 15:
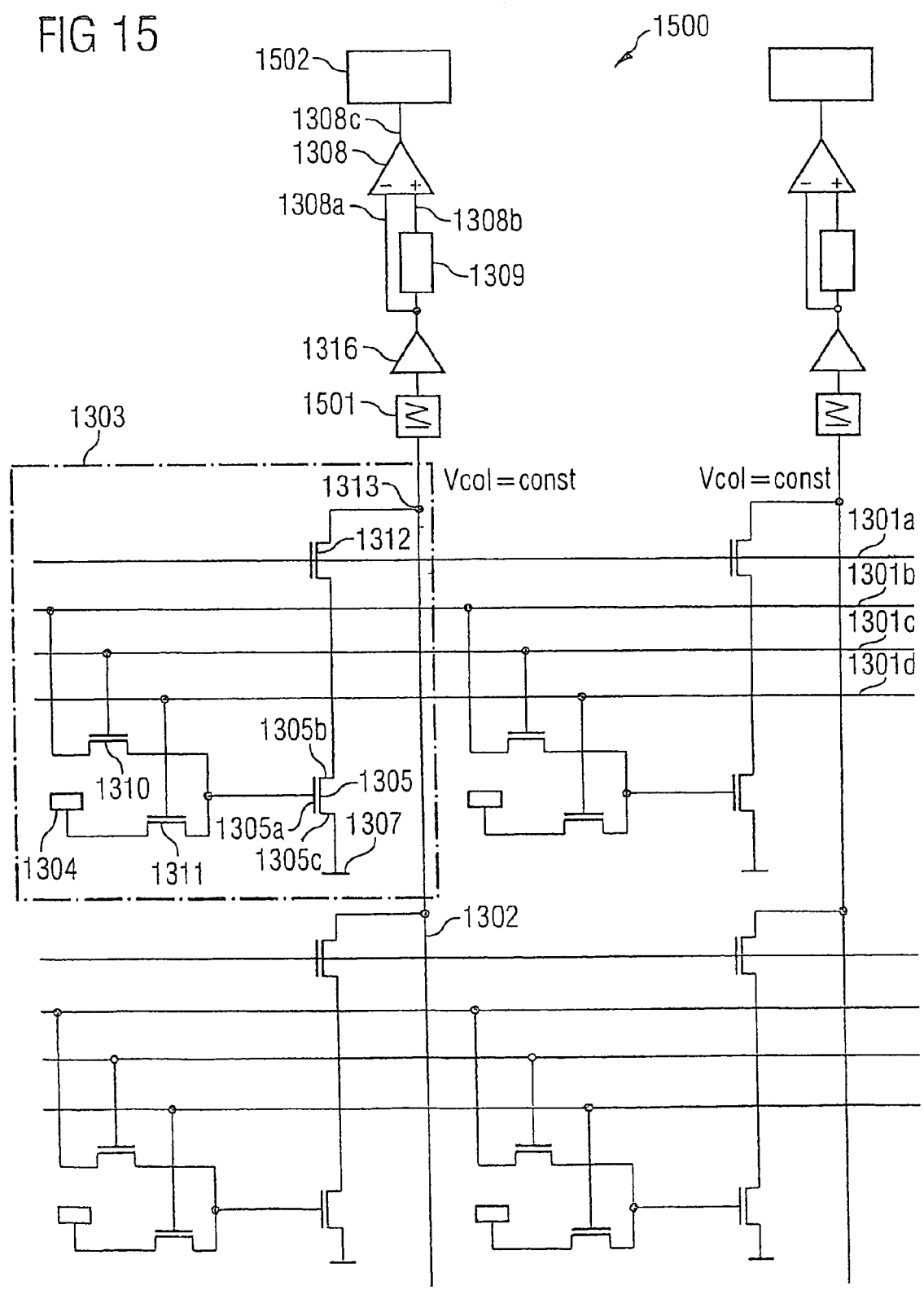

Reference is made below to FIG. 13 to FIG. 15 on the basis of which a description is given of a different concept which can be used to at least partly compensate for an alteration of the value of a physical parameter of a sensor element.

Firstly, the sensor array 1300 shown in FIG. 13 is described.

The sensor array 1300 has a plurality of biosensor circuit arrangements 1303 which are arranged essentially in matrix form in crossover regions of row lines 1301a, 1301b, 1301c, 1301d and column lines 1302 and are connected up to the row and column lines 1301*a*, 1301*b*, 1301*c*, 1301*d*, 1302. As already in the case of the exemplary embodiments described above, each biosensor circuit arrangement 1303 has a sensor element having a physical parameter and a calibration device which is set up in such a way that it can be used to at least partly compensate for an alteration of the value of the physical parameter of the sensor element. The sensor element of the biosensor circuit arrangement 1303 has an electrically conductive electrode 1304 that can be coupled to a substance to be examined (not shown in the figure). Furthermore, the sensor element of the biosensor circuit arrangement 1303 has a measuring transistor 1305, the gate terminal 1305*a* of which is coupled to the electrically conductive sensor electrode 1304 (via a further transistor 1311 described further below). Furthermore, in FIG. 13, a voltmeter 1306 for detecting an electrical sensor voltage is provided for each column line 1302, which voltmeter 1306 can be coupled to a first source/drain terminal 1305*b* of the measuring transistor 1305.

The calibration device of the biosensor circuit arrangement 1303 is set up in such a way that it can be used to convert a sensor signal of the sensor element, said sensor signal being brought about by the sensor event, using the principle of correlated double sampling (CDS), into a value which is independent of the value of the physical parameter of the sensor element.

In the case of the biosensor circuit arrangement 1303, an electrical ground potential 1307 is applied to a second source/drain terminal 1305*c* of the measuring transistor 1305. The calibration device has a differential amplifier 1308 having a first input 1308*a* and a second input 1308*b* and an output 1308*c*, which output 1308*b* is coupled to the voltmeter 1306, which first input 1308*a* can be coupled to the first source/drain terminal 1305*b* of the measuring transistor 1305, and which differential amplifier is set up in such a way that the difference between two electrical signals applied to the two inputs (the first, inverted input 1308*a* and the second, non-inverted input 1308*b*) can be provided at its output 1308*c*. Furthermore, the calibration device has a sample-and-hold element 1309 connected between the first source/drain terminal 1305*b* of the measuring transistor 1305 and the second input 1308*b* of the differential amplifier 1308. The calibration device is set up in such a way that, in a first operating state, a sensor signal dependent on the physical parameter of the sensor element (that is to say the threshold voltage of the measuring transistor 1305) can be impressed into the sample-and-hold element 1309 and can be provided to the second input 1308*b* of the differential amplifier 1308. Furthermore, the calibration device is set up in such a way that, in a second operating state, a signal that is characteristic of the physical parameter of the sensor element can be provided to the first input 1308*a* of the differential amplifier 1308. The calibration device is furthermore set up in such a way that a sensor signal, an electrical voltage, independent of the value of the physical parameter of the sensor element can be provided at the output 1308*c* of the differential amplifier 1308, as a result of which the alteration of the value of the physical parameter is at least partly compensated for.

Furthermore, the biosensor circuit arrangement 1303 has a first switching transistor 1310 and a second switching transistor 1311. The sensor electrode 1304 is coupled to the first source/drain terminal of the second switching transistor 1311, and the other source/drain terminal of the second switching transistor 1311 is coupled to the gate terminal 1305*a* of the measuring transistor 1305 and to the first source/drain terminal of the first switching transistor 1310. The second source/drain terminal of the first switching transistor 1310 is coupled to the second row line 1301*b*, and the gate terminal of the first switching transistor 1310 is coupled to the third row line 1301*c*. Furthermore, the gate terminal of the second switching transistor 1311 is coupled to the fourth row line 1301*d*. The biosensor circuit arrangement 1303 has a third switching transistor 1312, the first source/drain terminal of which is coupled to the first source/drain terminal 1305*b* of the measuring transistor 1305. The gate terminal of the third switching transistor 1312 is coupled to the first row line 1301*a*, and the second source/drain terminal of the third switching transistor 1312 is coupled to an electrical crossover point 1313, which is coupled to one terminal of a load element 1314, to the other terminal of which a supply voltage 1315 is applied. Furthermore, the electrical crossover point 1313 is coupled via an amplifier 1316 both to the inverted first input 1308*a* of the differential amplifier 1308 and to the sample-and-hold element 1309.

The principle of correlated double sampling, described for example in Enz, C C et al. (1996) "Circuit techniques for reducing the effects of op-amp imperfections: autozeroing, correlated double sampling, and chopper stabilization", Proceedings of the IEEE 84(11):1584ff, is explained below. The attenuation of most components and the suppression of the offset component are made possible in accordance with this concept. In this case, the input of an amplifier is often coupled to a signal source to be measured. At the output of the amplifier, the amplified signal plus an offset signal of the amplifier is then measured and stored. In a next phase, the amplifier is coupled to a suitable reference source. Only the offset component is then present at the output of the amplifier. The offset component of the amplifier can be eliminated by forming the difference between the two output voltages, thereby obtaining the signal free of the offset of the amplifier.

In order to operate the sensor array 1300 with the correlated double sampling concept, the rows of biosensor circuit arrangements 1303 are read successively. In order to read a row of biosensor circuit arrangements 1303, the associated first row line 1301*a* has applied to it an electrical signal such that the third switching transistor 1312 is thereby turned on. As a result, the first source/drain terminal 1305*b* of the measuring transistor 1305 is coupled to the read-out circuit in the upper region of the sensor array 1300 from FIG. 13. The actual measurement is effected in two places:

In the first phase, the fourth row line 1301*d* has applied to it an electrical signal such that the second switching transistor 1311 is thereby turned on. If the potential of the sensor electrode 1304 is altered on account of a sensor event at the sensor electrode 1304, then the Helmholtz layer at the sensor electrode 1304 and the gate capacitance of the measuring transistor 1305 form a voltage divider. In this connection, it should be noted that, in the electrical equivalent circuit diagram, a nonreactive resistance representing the electrical conductivity of the electrolyte may be connected in parallel with the Helmholtz layer. The term Helmholtz layer refers to a layer sequence of layers with alternately electrically charged particles that forms above an electrically charged electrode. Clearly, the ions are sorted in a plurality of layers, so that, by way of example, there is situated in the immediate vicinity of a positively charged electrode a layer with negatively charged ions, followed by a layer of positive ions somewhat further away from the electrode, then a layer of negative ions again, etc. The definiteness of the layers decreases with increasing distance from the electrode surface. Such a Helmholtz layer may be interpreted as a capacitance. Assuming that the capacitance of a Helmholtz layer is significantly greater than the capacitance at the gate terminal 1305a of the measuring transistor 1305, approximately the entire voltage is dropped across the gate terminal 1305a of the measuring transistor 1305. In this configuration, the measuring transistor 1305 is operated in a common source connection, and a change in the potential at the gate terminal 1305a brings about a change—amplified by a specific factor—in the potential at the first source/drain terminal 1305b. This gain factor depends on the product of the slope of the transistor characteristic curve of the measuring transistor 1305 and the value of the resistance. This voltage change is amplified by means of the amplifier 1316 outside the biosensor circuit arrangement 1303, a common amplifier 1316 in each case being formed for each column line 1302. Both the measuring transistor 1035 and the amplifier 1316 have an offset which is added to the sensor signal. The output voltage of the amplifier 1316 is stored in the sample-and-hold element 1309.

The electrical signal applied to the fourth row line 1301d is then removed, so that the second switching transistor 1311 turns off.

In the second phase of the measurement, the third row line 1301c has applied to it an electrical signal such that the first switching transistor 1310 turns on. The reference voltage applied to the second row line 1301b is then applied to the gate terminal 1305a of the measuring transistor 1305. In this case, only the above-described offset of the measuring transistor 1305 or of the amplifier 1316 itself is present at the output of the amplifier 1316. Therefore, the sensor signal plus the offset component from the first measurement phase is present at the non-inverted input 1308b of the differential amplifier 1308, whereas solely the offset component from the second measurement phase is present at the inverted first input 1308a of the differential amplifier 1308. The differential signal between the inputs 1308a, 1308b of the differential amplifier 1308 is therefore the pure sensor signal without the offset component. The alteration of the value of the physical parameter of the sensor element of the biosensor circuit arrangement 1303 is thereby compensated for.

In the text below reference is made to FIG. 14 and a description is given of a thirteenth preferred exemplary embodiment of the sensor array according to the invention.

The sensor array 1400 shown in FIG. 14 differs from the sensor array 1300 shown in FIG. 13 by the fact that the load element 1314, an electrical resistor, is replaced by a constant-current source 1401. In the case of the sensor array 1400, the correlated double sampling principle is analogous to that in the case of the sensor array 1300, the amplification of the change in the gate voltage at the measuring transistor 1305 now resulting from the quotient of transconductance and output conductance of the measuring transistor 1305.

FIG. 15 shows a sensor array 1500 in accordance with a fourteenth exemplary embodiment of the invention.

The sensor array 1500 represents another modification of the sensor array 1300 from FIG. 13. In the case of the exemplary embodiment of FIG. 15, the load element 1314 and a supply voltage 1315 are dispensable, but a current-voltage converter 1501 is connected between the node 1313 and the amplifier 1316. The current-voltage converter 1501 is formed jointly for all the biosensor circuit arrangements 1303 of a column line 1302.

In other words, in accordance with the exemplary embodiment of the sensor array 1500 according to the invention as shown in FIG. 15, a voltage signal rather than a current signal is read out by means of the measuring transistor 1305. In this case, the electrical voltage $V_{col}$ on the column lines 1302 is kept constant, that is to say that it is not necessary to reverse the charge of parasitic capacitances, and the circuit can be read faster. The change in the current flow through the first source/drain terminal 1305b of the measuring transistor 1305 is converted into an electrical voltage by means of the current-voltage converter 1501. In accordance with the exemplary embodiment shown in FIG. 15, too, the difference between the amplified measurement signal and the amplified reference signal is formed, the latter reflecting the offset of the measuring transistor 1305 on account of an alteration of the threshold voltage, and, in this case, too, the offset quantities do not affect the output signal of the differential amplifier 1308 at the output 1308c. The sensor voltage signal may be detected for example by means of a voltmeter 1502.

It must be emphasized that the principle of correlated double sample (CDS) can also be realized by means of a more complex amplifier device for example based on differential stages, etc.

The exemplary embodiments of the sensor array according to the invention as described with reference to FIG. 2 to FIG. 15 in each case relate to a scenario in which an individual biosensor circuit arrangement is selectively selected in order to detect its sensor signal. A description is given below, with reference to FIG. 16 to FIG. 19, of exemplary embodiments of the sensor array according to the invention in which summation currents of individual sensor currents of biosensor circuit arrangements of a row line or a column line are detected.

Figure 16:
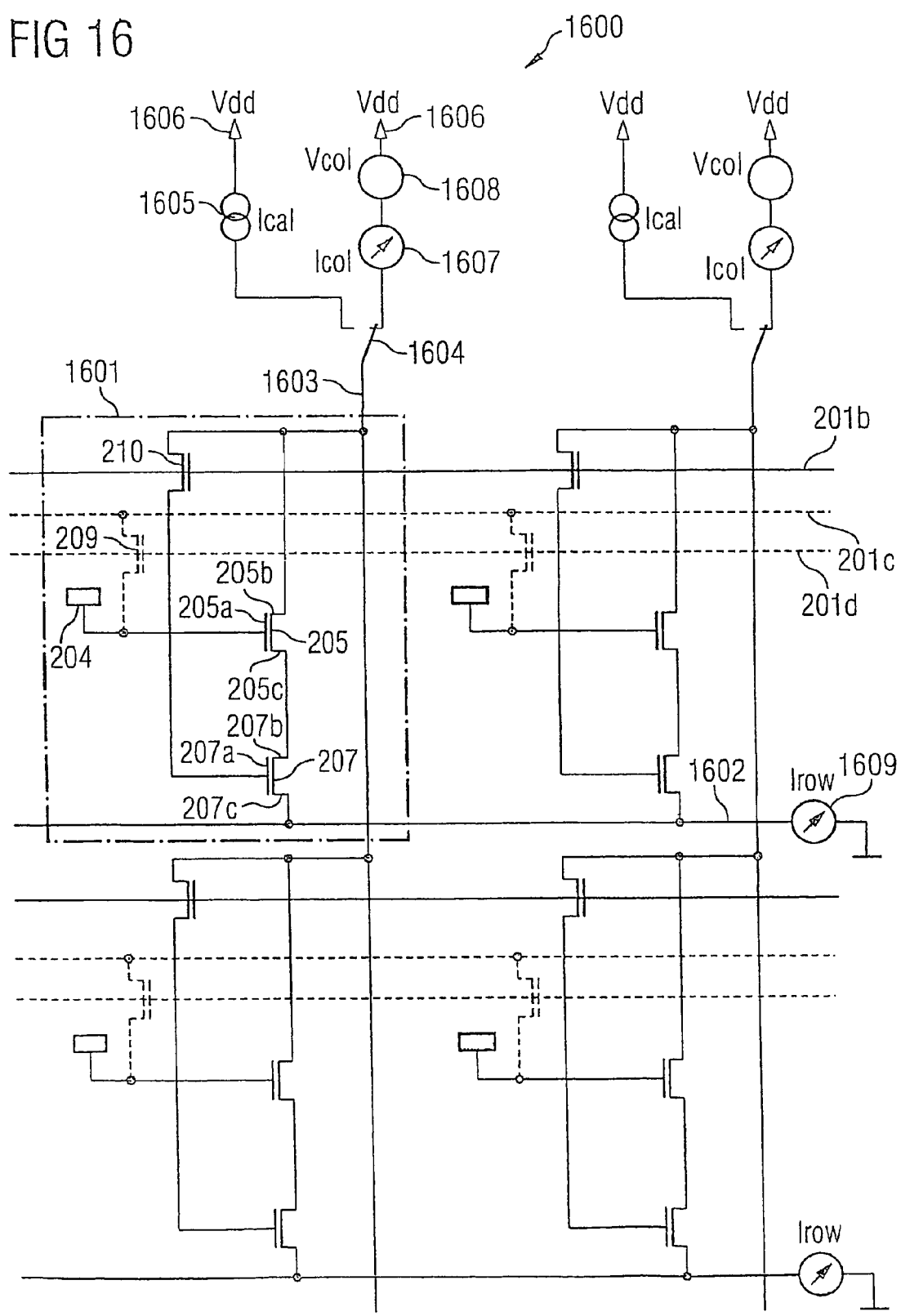

FIG. 16 shows a sensor array 1600 having a plurality of biosensor circuit arrangements 1601 which are arranged essentially in matrix form in crossover regions of row lines 201b, 201c, 201d and 1602 and column lines 1603 and are connected up to the row and column lines 201b, 201c, 201d, 1602, 1603.

The biosensor circuit arrangements 1600 are configured like the biosensor circuit arrangements 203 shown in FIG. 2 with the difference that, in accordance with the exemplary embodiment shown in FIG. 16, a first row line 201a is dispensable since, in accordance with this exemplary embodiment, a summation current of a plurality of biosensor circuit arrangements 1601 arranged along a row or column is detected. Selection of a biosensor circuit arrangement of a column line 1603 is therefore not necessary in FIG. 16. Instead, a summation current row line 1602 is formed, which is coupled to the second source/drain terminals 207c of the calibration transistor 207 of a row of biosensor circuit arrangements 1601. Along a summation current column line 1603, the individual sensor current signals of the biosensor circuit arrangements 1601 of the associated column accumulate at a switch 1604 in an end section of each column line 1603. One terminal of a constant-current source 1605 is coupled to the switch 1604, a supply voltage 1606 being applied to the other terminal of said constant-current source. Furthermore, the switch 1604 is coupled to a first ammeter 1607, which is in turn coupled to a voltage source 1608, to one terminal of which the potential of a supply voltage 1606 is applied. Furthermore, a second ammeter 1609 is arranged at an end section of each summation current column line 1602.

Thus, in the case of the sensor array 1600 shown in FIG. 16, unlike in the exemplary embodiment described above, a specific biosensor circuit arrangement 1601 per column line 1603 is not selected, rather summation currents of a plurality of biosensor circuit arrangements 1601 along a summation current row line 1602 or along a summation current column line 1603 are instead detected and evaluated. In order to compensate for parameter fluctuations of the measuring transistor 205 in different biosensor circuit arrangements 1601, the calibration transistors 207 are switched into the current path, an electrical charge for compensating for an alteration of the value of a physical parameter of a sensor element (or of a measuring transistor 205) being applied to the gate terminals 207a of the calibration transistors 207 in a calibration phase.

In a calibration phase, the switch 1604 is placed such that the summation current column line 1603 is coupled to the constant-current source 1605. In other words, a predefined current $I_{cal}$ is impressed into a biosensor circuit arrangement 1601 of a column line 1603, which biosensor circuit arrangement 1601 is selected by means of an electrical signal on the second row line 201b, which signal has the effect that the second switching transistor 210 turns on. In the case of a predetermined electrical voltage on the summation current row line 1602, the second source/drain terminals 207c of the calibration transistors 207b of a row of biosensor circuit arrangements 1601 are coupled, and a voltage is established at the gate terminal 207a of the calibration transistor 207, which voltage puts the biosensor circuit arrangement 1601 to be calibrated into a state to carry precisely the impressed current. The calibration transistor 207 once again brings about a source negative feedback of the measuring transistor 205. If a calibration charge has been established at the gate terminal 207a, then the electrical signal on the second row line 201b, by means of which signal the second switching transistor 210 had previously been turned on, is switched off, so that the second switching transistor 210 turns off. However, the charge applied during the calibration phase remains on the gate capacitance of the calibration transistor 207, so that the electrical potential at the gate terminal 207a of the calibration transistor 207 remains unchanged. As a result, the associated biosensor circuit arrangement is calibrated.

During measurement operation, the switch 1604 is brought to the position shown in FIG. 16, that is to say to the complementary position with respect to the position set during the calibration phase, and an electrical signal which would turn on the second switching transistor 210 is present on none of the second row lines 201b. Changes in the potential at the sensor electrode 204 V(E) lead to a change in the current through the first source/drain terminal 205b of the measuring transistor 205 and therefore to a change in the contribution of a biosensor circuit arrangement 1601 to the summation currents in the assigned summation current row line 1602 or summation current column line 1603.

Figure 17:
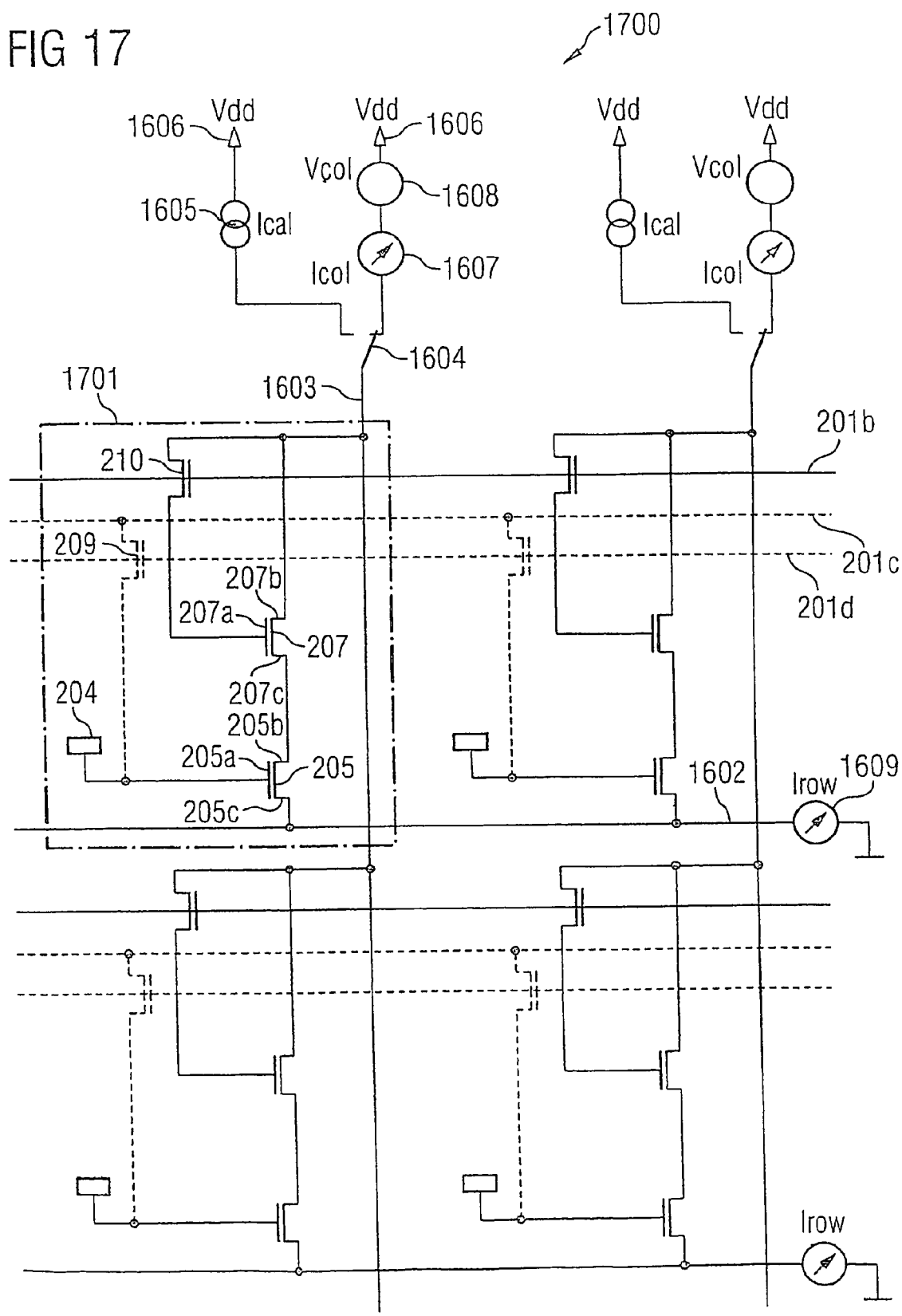

FIG. 17 shows a sensor array 1700 in accordance with a sixteenth exemplary embodiment of the invention.

The sensor array 1700 differs from the sensor array 1600 shown in FIG. 16 merely by the fact that, in contrast to FIG. 16, the biosensor circuit arrangement 1701 is not configured as source negative feedback, but rather in accordance with the manner shown in FIG. 4, namely in such a way that the calibration transistor 207 is formed as a source follower. In other words, in the case of FIG. 17, the calibration is not effected by means of a source negative feedback of the measuring transistor 205 by the calibration transistor 207, rather the calibration transistor 207 is in this case an element for setting the potential of the first source/drain terminal 205b of the measuring transistor 205.

Figure 18:
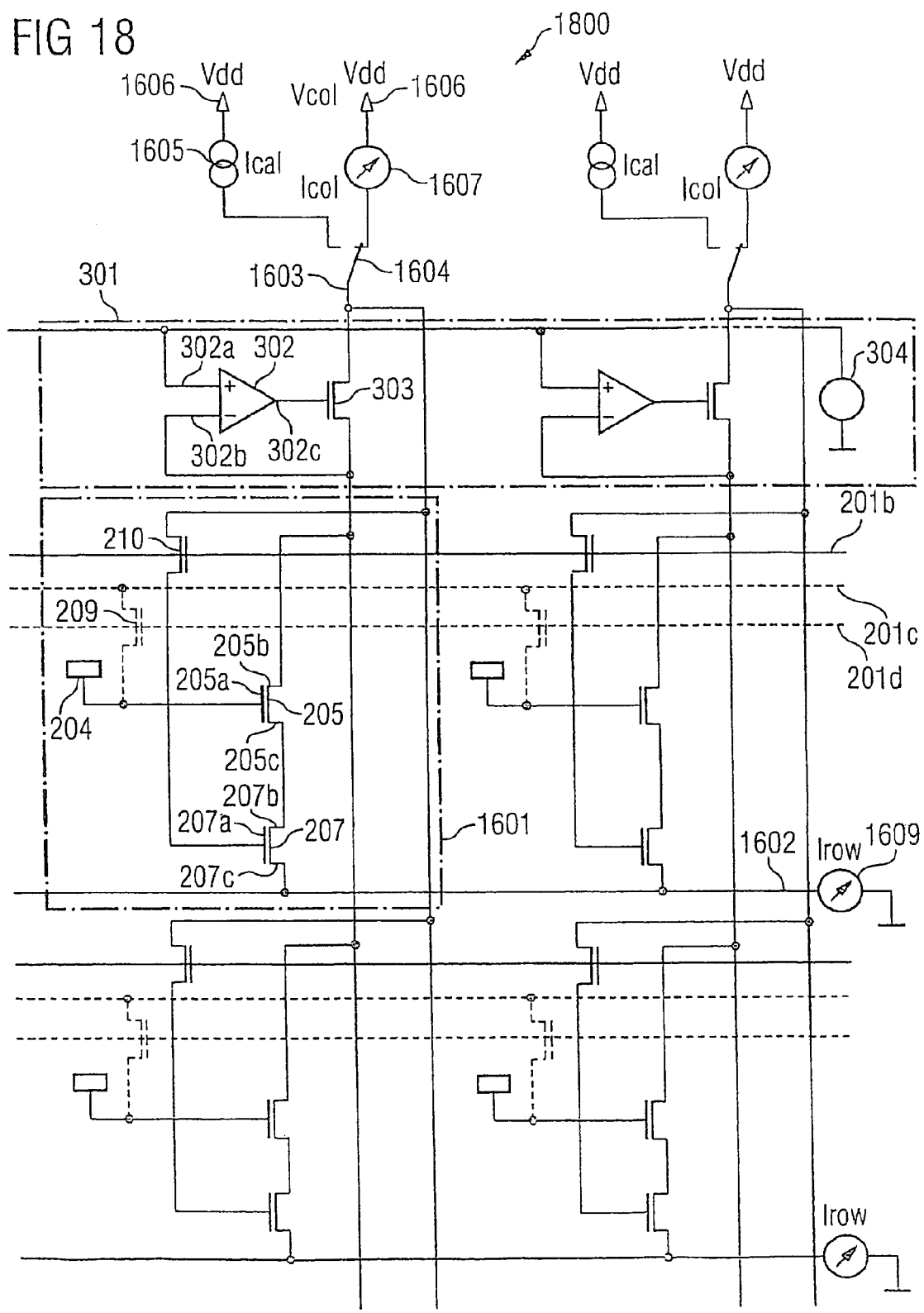

FIG. 18 shows a sensor array 1800 in accordance with a seventeenth exemplary embodiment of the invention. The sensor array 1800 largely corresponds to the sensor array 1600 shown in FIG. 16, but additionally has a potential control device 301, which is described in detail above with reference to FIG. 3. By means of the potential control device 301, the electrical potential of the signal-carrying column lines 1603 can be kept constant both during the calibration phase and during the measurement phase.

Figure 19:
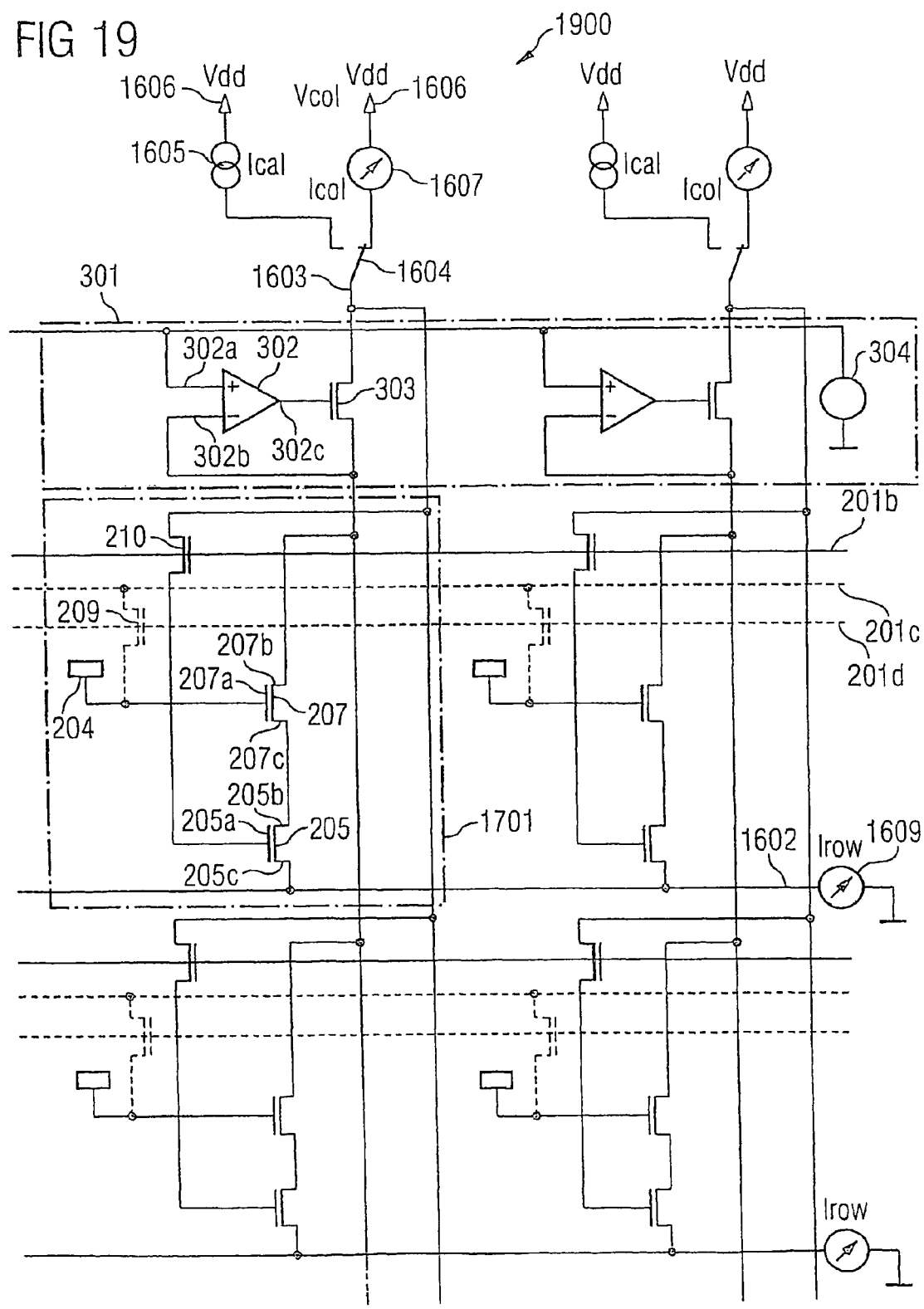

FIG. 19 shows a sensor array 1900 in accordance with an eighteenth exemplary embodiment of the invention.

The exemplary embodiment shown in FIG. 19 corresponds to the exemplary embodiment shown in FIG. 17, a potential control device 301 for keeping the electrical potential of the current-carrying column line 1603 constant additionally being provided.

The evaluation of summation current signals in accordance with the sensor arrays of FIG. 16 to FIG. 19 is effected for example using a correlation calculation described below. Firstly, for at least a portion of the summation current row lines 1602 and the summation current column lines 1603, the respective summation current of the respective row line and column line is detected, which summation current contains individual currents of the biosensor circuit arrangements arranged along one of the associated lines. Since a sensor event occurs in a biosensor circuit arrangement in a crossover region of a row line and a column line in correlated fashion in these two lines, those biosensor circuit arrangements at which a sensor event has been effected can be deduced from the summation currents. In particular, for this purpose, the time-dependent summation currents of the row lines and of the column lines can be subjected to Fourier transformation, the Fourier-transformed summation currents in each case of a row line and in each case of a column line can be multiplied together in pairs and the product can be subjected to an inverse Fourier transformation. From the current products that have been subjected to inverse Fourier transformation, a possible correlation between a summation current signal of a row line and a column line can be determined, and it is possible to determine whether or not a sensor event has taken place at the biosensor circuit arrangement in the respective crossover region of the row and column lines used for the correlation calculation.

The invention claimed is:

1. A biosensor circuit arrangement comprising:
    a substrate;
    a sensor element formed in or on a surface region of the substrate with a physical parameter, which is coupled to a substance to be examined, the type of coupling having a resistive component, the sensor element having an electrically conductive sensor electrode that is coupled to the substance to be examined, the sensor element having a measuring transistor the gate terminal of which is coupled to the electrically conductive sensor electrode, and the physical parameter being the threshold voltage of the measuring transistor; and
    a calibration device formed in or on the substrate, said calibration device being set up such that it is used to at least partly compensate for an alteration of the value of the physical parameter of the sensor element.

2. The biosensor circuit arrangement as claimed in claim 1, further comprising a device for detecting an electrical parameter characterizing an effected sensor event, the device being coupled to a first source/drain terminal of the measuring transistor.

3. The biosensor circuit arrangement as claimed in claim 2, wherein the calibration device is set up such that it is used to control the electrical potential applied to the first or a second source/drain terminal of the measuring transistor in such a way that it can set a sensor signal of the sensor element, said sensor signal being brought about by a sensor event, to a value which is independent of the value of the physical parameter of the sensor element.

4. The biosensor circuit arrangement as claimed in claim 3, wherein the calibration device is set up such that it is used to control the electrical potential present at the first source/drain terminal of the measuring transistor.

5. The biosensor circuit arrangement as claimed in claim 4, wherein a first electrical reference potential is applied to the second source/drain terminal of the measuring transistor, and in which the calibration device has a calibration transistor having a first and a second source/drain terminal, which are connected between the first source/drain terminal of the measuring transistor and the device for detecting an electrical parameter, and to the gate terminal thereof an electrical signal is applied such that the electrical potential which is applied to the first source/drain terminal of the measuring transistor is set such that the alteration of the value of the physical parameter of the sensor element can at least partly be compensated for.

6. The biosensor circuit arrangement as claimed in claim 4, wherein the calibration device is set up such that it is used to control the electrical potential present at the second source/drain terminal of the measuring transistor.

7. The biosensor circuit arrangement as claimed in claim 6, wherein the first source/drain terminal of the measuring transistor is coupled to the device for detecting an electrical parameter, and wherein the calibration device has a calibration transistor having a first source/drain terminal, which is coupled to the second source/drain terminal of the measuring transistor, and a second source/drain terminal, to which a second electrical reference potential is applied, and to the gate terminal of which an electrical signal is applied such that the electrical potential which is applied to the second source/drain terminal of the measuring transistor is set such that the alteration of the value of the physical parameter of the sensor element can at least partly be compensated for.

8. The biosensor circuit arrangement as claimed in claim 6, wherein the calibration device comprises:
   a calibration transistor;
   a first constant-current source, which is coupled to respective second source/drain terminals of the measuring and calibration transistors that are connected in parallel with one another, for the provision of a predeterminable electrical current intensity; and
   a current mirror circuit, which is coupled to respective first source/drain terminals of the measuring and calibration transistors that are connected in parallel with one another, and which is connected such that it is used to set, for at least partly compensating for the alteration of the value of the physical parameter, the electrical potential at the gate terminal of the calibration transistor such that, in the absence of a sensor event, the current flows between the two source/drain terminals of the measuring transistor and of the calibration transistor are identical.

9. The biosensor circuit arrangement as claimed in claim 6, wherein a third electrical reference potential is applied to the first source/drain terminal of the measuring transistor, and wherein the calibration device comprises:
   a calibration transistor having a first and a second source/drain terminal;
   a second constant-current source, which is coupled to the respective second source/drain terminals of the measuring and calibration transistors that are connected in parallel with one another, for the provision of a predeterminable electrical current intensity; and
   a third constant-current source, which is coupled to the first source/drain terminal of the calibration transistor, for the provision of a further predeterminable electrical current intensity, the third constant-current source being connected such that it is used to set, for at least partly compensating for the alteration of the value of the physical parameter, the potentials that are applied to the terminals of the transistors such that, in the absence of a sensor event, the current flows between the two source/drain terminals of the measuring transistor and of the calibration transistor are identical.

10. The biosensor circuit arrangement as claimed in claim 2, wherein the calibration device is set up such that it is used to convert a sensor signal of the sensor element, said sensor signal being brought about by a sensor event, using a principle of correlated double sampling to a value which is independent of the value of the physical parameter of the sensor element.

11. The biosensor circuit arrangement as claimed in claim 10, wherein a fourth electrical reference potential is applied to a second source/drain terminal of the measuring transistor;
   wherein the calibration device comprises:
      an electrical subtraction device having two inputs and an output, which is coupled to the device for detecting an electrical parameter, a first one of the two inputs is coupled to the first source/drain terminal of the measuring transistor, and the electrical subtraction device is set up such that a difference between two electrical signals applied to the two inputs is provided at its output; and
      a sample-and-hold element connected between the first source/drain terminal of the measuring transistor and the second input of the electrical subtraction device; and
   wherein the calibration device is set up such that:
      in a first operating state, a sensor signal dependent on the physical parameter of the sensor element is impressed into the sample-and-hold element and is provided to the second input of the electrical subtraction device;
      in a second operating state, a signal which is characteristic of the physical parameter of the sensor element is provided to the input of the electrical subtraction device; and
      a sensor signal independent of the value of the physical parameter of the sensor element is provided at the output of the electrical subtraction device, as a result of which the alteration of the value of the physical parameter is at least partly compensated for.

12. The biosensor circuit arrangement as claimed in claim 11, further comprising a switching device set up such that it is used optionally to couple the sensor element to a fifth electrical reference potential or to decouple it from the latter, in order to protect the sensor element from damage.

13. The biosensor circuit arrangement as claimed in claim 11, further comprising a switching device set up such that it is used optionally to couple the sensor element to a fifth electrical reference potential or to decouple it from the latter, in order to apply a defined electrical potential to the sensor element.

14. The biosensor circuit arrangement as claimed in claim 11, further comprising a switching device set up such that it is used optionally to couple the sensor element to a fifth electrical reference potential or to decouple it from the latter, in order to protect the sensor element from damage and in order to apply a defined electrical potential to the sensor element.

15. The biosensor circuit arrangement as claimed in claim 2, wherein the electrical parameter is an electrical voltage or an electric current.

16. The biosensor circuit arrangement as claimed in claim 1, wherein the sensor electrode has one or a combination of materials selected from the group consisting of titanium, titanium nitride, gold, and platinum.

17. The biosensor circuit arrangement as claimed in claim 1, further comprising an amplifier element for amplifying a sensor signal.

18. The biosensor circuit arrangement as claimed in claim 1, wherein the substrate is a silicon substrate.

19. The biosensor circuit arrangement as claimed in claim 1, wherein a type of coupling between the sensor element and a liquid to be examined has a capacitive component.

20. A sensor array having a plurality of biosensor circuit arrangements as claimed in claim 1, wherein said biosensor circuit arrangements are arranged essentially in matrix form in crossover regions of row and column lines and being connected up to the row and column lines.

21. The sensor array as claimed in claim 20, wherein at least a portion of the biosensor circuit arrangements have a selection element—coupled to the respectively associated row line and column line—for selection of the respective sensor arrangement to detect a sensor signal of the sensor element of the selected biosensor circuit arrangement and, in the case of the selected biosensor circuit arrangement, at least partly to compensate for the alteration of the value of the physical parameter.

22. The sensor array as claimed in claim 20, wherein at least a portion of the column lines are coupled to a potential control device, which is set up such that it holds the electrical potential of the associated column line at an essentially constant value.

23. A biosensor array having a sensor array as claimed in claim 20.

24. The sensor array as claimed in claim 20, wherein at least a portion of the biosensor circuit arrangements have a selection element—coupled to the respectively associated row line and column line—for selection of the respective sensor arrangement to detect a sensor signal of the sensor element of the selected biosensor circuit arrangement and, in the case of the selected biosensor circuit arrangement, to apply a fifth electrical potential to the sensor element of the selected biosensor circuit arrangement.

25. The sensor array as claimed in claim 20, wherein at least a portion of the biosensor circuit arrangements have a selection element—coupled to the respectively associated row line and column line—for selection of the respective sensor arrangement to detect a sensor signal of the sensor element of the selected biosensor circuit arrangement and, in the case of the selected biosensor circuit arrangement, at least partly to compensate for the alteration of the value of the physical parameter and to apply a fifth electrical potential to the sensor element of the selected biosensor circuit arrangement.

26. The sensor array as claimed in claim 20, wherein at least a portion of the biosensor circuit arrangements have a selection element—coupled to the respectively associated row line and column line—for selection of the respective sensor arrangement to detect a sensor signal of the sensor element of the selected biosensor circuit arrangement or, in the case of the selected biosensor circuit arrangement, at least partly to compensate for the alteration of the value of the physical parameter.

27. The sensor array as claimed in claim 20, wherein at least a portion of the biosensor circuit arrangements have a selection element—coupled to the respectively associated row line and column line—for selection of the respective sensor arrangement to detect a sensor signal of the sensor element of the selected biosensor circuit arrangement or, in the case of the selected biosensor circuit arrangement, to apply a fifth electrical potential to the sensor element of the selected biosensor circuit arrangement.

28. The sensor array as claimed in claim 20, wherein at least a portion of the biosensor circuit arrangements have a selection element—coupled to the respectively associated row line and column line—for selection of the respective sensor arrangement to detect a sensor signal of the sensor element of the selected biosensor circuit arrangement or, in the case of the selected biosensor circuit arrangement, at least partly to compensate for the alteration of the value of the physical parameter and to apply a fifth electrical potential to the sensor element of the selected biosensor circuit arrangement.

29. The sensor array as claimed in claim 20, wherein at least a portion of the biosensor circuit arrangement assigned to a respective row line comprises a common device for detecting an electrical parameter that characterizes an effected sensor event, a common constant-current source, a common switching device, a common reference potential, a common current-voltage converter, a common analog-digital converter, a common current mirror, a common subtraction device, a common sample-and-hold element, and a common amplifier.

30. The sensor array as claimed in claim 20, wherein at least a portion of the biosensor circuit arrangement assigned to a respective row line comprises a common device for detecting an electrical parameter that characterizes an effected sensor event, a common constant-current source, a common switching device, a common reference potential, a common current-voltage converter, a common analog-digital converter, a common current mirror, a common subtraction device, a common sample-and-hold element, or a common amplifier.

31. The sensor array as claimed in claim 20, wherein at least a portion of the biosensor circuit arrangement assigned to a respective column line comprises a common device for detecting an electrical parameter that characterizes an effected sensor event, a common constant-current source, a common switching device, a common reference potential, a common current-voltage converter, a common analog-digital converter, a common current mirror, a common subtraction device, a common sample-and-hold element, and a common amplifier.

32. The sensor array as claimed in claim 20, wherein at least a portion of the biosensor circuit arrangement assigned to a respective column line comprises a common device for detecting an electrical parameter that characterizes an effected sensor event, a common constant-current source, a common switching device, a common reference potential, a common current-voltage converter, a common analog-digital converter, a common current mirror, a common subtraction device, a common sample-and-hold element, or a common amplifier.

33. The sensor array as claimed in claim 20, wherein at least a portion of the row lines in each case have a device for detecting an electrical parameter that characterizes and effected sensor event, the sensor array being set up such that the device for detecting and electrical parameter that is assigned to a respective row or column line can detect a sensor signal of precisely one sensor arrangement of the respective row or column line, or a sum of sensor signals of at least a portion of the sensor arrangement of the respective row or column line.

34. The sensor array as claimed in claim 20, wherein at least a portion of the column lines in each case have a device for detecting an electrical parameter that characterizes an effected sensor event, the sensor array being set up such that the device for detecting an electrical parameter that is assigned to a respective row or column line can detect a sensor signal of precisely one sensor arrangement of the respective row or column line, or a sum of sensor signals of at least a portion of the sensor arrangement of the respective row or column line.

35. The sensor array as claimed in claim 20, wherein at least a portion of the row lines and the column lines in each case have a device for detecting an electrical parameter that characterizes an effected sensor event, the sensor array being set up such that the device for detecting an electrical parameter that is assigned to a respective row or column line can detect a sensor signal of precisely one sensor arrangement of the respective row or column line, or a sum of sensor signals of at least a portion of the sensor arrangement of the respective row or column line.

* * * * *

UNITED STATES PATENT AND TRADEMARK OFFICE
CERTIFICATE OF CORRECTION

| | | |
|---|---|---|
| PATENT NO. | : 7,019,305 B2 | Page 1 of 1 |
| APPLICATION NO. | : 10/821803 | |
| DATED | : March 28, 2006 | |
| INVENTOR(S) | : Bjorn-Oliver Eversmann et al. | |

It is certified that error appears in the above-identified patent and that said Letters Patent is hereby corrected as shown below:

Column 36, line 63, "and" should read --an--; and

Column 36, line 65, "and" should read --an--.

Signed and Sealed this

Third Day of October, 2006

JON W. DUDAS
*Director of the United States Patent and Trademark Office*